(12) United States Patent
Gambone et al.

(10) Patent No.: US 7,521,207 B2
(45) Date of Patent: Apr. 21, 2009

(54) RHESUS MONKEY NUR77

(75) Inventors: Carlo J. Gambone, Norristown, PA (US); Azriel Schmidt, Bryn Mawr, PA (US)

(73) Assignee: Merck & Co., Inc., Rahway, NJ (US)

( * ) Notice: Subject to any disclaimer, the term of this patent is extended or adjusted under 35 U.S.C. 154(b) by 4 days.

(21) Appl. No.: 11/377,734

(22) Filed: Mar. 16, 2006

(65) Prior Publication Data

US 2006/0223123 A1  Oct. 5, 2006

Related U.S. Application Data

(60) Provisional application No. 60/662,197, filed on Mar. 16, 2005.

(51) Int. Cl.
C12P 21/06 (2006.01)
C12N 5/00 (2006.01)
C12N 15/00 (2006.01)
C07H 21/04 (2006.01)

(52) U.S. Cl. .................. 435/69.1; 435/325; 435/320.1; 536/23.5; 536/23.1

(58) Field of Classification Search .................. None
See application file for complete search history.

(56) References Cited

U.S. PATENT DOCUMENTS

2002/0049151 A1* 4/2002 Murphy et al. .................. 514/1
2003/0220288 A1* 11/2003 Mullican et al. .............. 514/44

FOREIGN PATENT DOCUMENTS

WO   WO 01/87923   * 11/2001

OTHER PUBLICATIONS

Pichon et al. 1996. Endocrinology 137:4691-4698.*
Hsu et al. 2004. Current Drug Targets- Inflammation and Allergy. 3:413-423.*
Aarnisale, et al., "Defining Requirements for Heterodimerization between the Retinoid X Receptor and the Orphan Nuclear Receptor Nurr1", J. of Biol. Chem., vol. 277, No. 38, pp. 35118-35123, Sep. 2002.
Cao, et al., "Retinoid X Receptor Regulates Nur77/Thyroid Hormone Receptor 3-Dependent Apoptosis by Modulating Its Nuclear Export and Mitochondrial Targeting", Mol. and Cell Biol, Nov. 2004, pp. 9705-9725.
Davis, et al., "Endocrine and Neurogenic Regulation of the Orphan Nuclear Receptors Nurr77 and Nurr-1 in the Adrenal Glands", Mol. and Cell Biol., vol. 14, No. 5, May 1994, pp. 3469-3483.
Forman, et al, "Unique Response Pathways Are Established By Allosteric Interactions Among Nuclear Hormone Receptors", Cell, vol. 81, May 19, 1995, pp. 541-550.
Hazel, et al., "A Gene Inducible By Serum Growth Factors Encodes A Member Of The Steroid And Thyroid Hormone Receptor Superfamily", Proc. Natl. Acad. Sci., USA, vol. 85, Nov. 1988, pp. 8444-8448.
Hedvat, et al., "The Isolation and Characterization of MINOR, a Novel Mitogen-Inducible Nuclear Orphan Receptor", Mol. Endo., vol. 9, No. 12, 1995, pp. 1692-1700.
Holmes, et al., Comparison of the Mechanism of Induction of Apoptosis in Ovarian Carcinoma Cells by the Conformationally Restricted Synthetic Retinoids CD437 and 4-HPR, J. of Cell. Biochem., vol. 89, 2003, pp. 262-278.
Kolluri, et al., "Mitogenic Effect of Orphan Receptor TR3 and Its Regulation by MEKK1 in Lung Cancer Cells", Mol and Cell Biol., vol. 23, No. 23, Dec. 2003, pp. 8651-8667.
Maruyama, et al., "Expression of NOR-1 and its closely related members of the steroid/tyroid hormone receptor superfamily in human neuroblastoma cell lines," Cancer Letters, vol. 96, 1995, pp. 117-122.
Milbrandt, et al., "Nerve Growth Factor Induces a Gene Homologous to the Glucocorticoid Receptor Gene", Neuron, vol. 1, May 1988, pp. 183-188.
Murphy, et al., "Differential Regulation of Transcription by the NURR1/NUR77 Subfamily of Nuclear Transcription Factors", Gene Expression, vol. 5, 1996, p. 169-179.
Nakai, et al., "A Human Early Response Gene Homologous to Murine Nur77 and Rat NGFI-B, and Related to the Nuclear Receptor Superfamily", Mol. Endo., vol. 4, No. 10, 1990, pp. 1438-1443.
Ohkura, et al., "Molecular Cloning of a Novel Thyroid/Steroid Receptor Superfamily Gene From Cultured Rat Neuronal Cells", Biochem. and Biophys. Res. Comm., vol. 205, No. 3, 1994, pp. 1959-1965.
Okabe, et al., "Nur77, a member of the steroid receptor superfamily, antagonizes negative feedback of ACTH synthesis and secretion by glucocorticoid in pituitary corticotrope cells", J. of Endocrinology, vol. 156, 1998, pp. 169-175.
Perlmann, et al., "A novel pathway for vitamin A signaling mediated by RXR heterodimerization with NGFI-B and NURR1", Genes & Development, vol. 9, 1995, pp. 769-782.
Perlmann, et al., "Two Distinct Dimerization Interfaces Differentially Modulate Target Gene Specificity of Nuclear Hormone Receptors", Molecular Endocrinology, vol. 10, No. 8, 1996, pp. 958-966.
Phillips, et al., "Antagonism between Nur77 and Glucocorticoid Receptor for Control of Transcription", Mol. and Cell Biol., vol. 17, No. 10, Oct. 1997, pp. 5952-5959.

(Continued)

*Primary Examiner*—Manjunath Rao
*Assistant Examiner*—Shulamith H Shafer
(74) *Attorney, Agent, or Firm*—Maria V. Marucci; Valerie J. Camara

(57) ABSTRACT

The *Macaca mulatta* (rhesus monkey) Nur77 (rhNur77) nuclear receptor and the nucleic acid encoding the rhNur77 nuclear receptor are described. Further described are methods for identifying analytes that modulate expression or activity of the rhNur77 nuclear receptor. Analytes that affect Nur77 expression or activity may be used to treat or inhibit inflammatory diseases, for example, osteoarthritis and various bone, neurological, and prostrate disorders. The rhNur77 may also be used to treat various cancers, for example, prostate, ovarian, colon, lung, and gastric cancer.

13 Claims, 11 Drawing Sheets

OTHER PUBLICATIONS

Ryseck, et al., "Structure, mapping and expression of a growth factor inducible gene encoding a putative nuclear hormonal binding receptor", The EMBO Journal, vol. 8, No. 11, 1969, pp. 3327-3335.

Song, et al., "LH Induces Orphan Nuclear Receptor Nur77 Gene Expression in Testicular Leydig Cells", Endocrinology, vol. 142, No. 12, 2001, pp. 5116-5123.

Tetradis, et al., "Regulation of the Nuclear Orphan Receptor Nur77 in Bone by Parathyroid Hormone", Biochem. and Biophys. Res Comm., vol. 281, 2001, pp. 913-916.

Watson, et al., "The NGFI-B Gene, a Transcriptionally Inducible Member of the Steroid Receptor Gene Superfamily: Genomic Structure and Expression in Rat Brain after Seizure Induction", Mol. and Cell. Biol., vol. 9, No. 10, Oct. 1989, pp. 4213-4219.

Wilson, et al., "TR3/Nurr77 in Colon Cancer Cell Apoptosis", Cancer Research, vol. 63, 2003, pp. 5401-5407.

Wilson, et al., "Identification of the DNA Binding Site for NGFI-B by Genetic Selection in Yeast", Science, vol. 252, 1991, pp. 1296-1300.

Wilson, et al., "The Orphan Nuclear Receptor NGFI-B Regulates Expression of the Gene Encoding Steroid 21-Hydroxylase", vol. 13, No. 2, Feb. 1993, pp. 861-868.

Wilson, et al., "The Orphan Receptors BGFI-B an Steroidogenic Factor 1 Establish Monomer Binding as a Third Paradigm of Nuclear Receptor-DNA Interaction", Mol. and Cell. Biol., vol. 13, No. 9. Sep. 1993, pp. 5794-5804.

Winoto, et al., "Nuclear Hormone Receptors in T Lymphocytes", Cell, vol. 109, Apr. 2002, pp. S57-S66.

Wu, et al., "Promyelocytic leukemia protein PML inhibits Nur77-mediated transcription through specific functional interactions", Oncogene, vol. 21, 2002, pp. 3925-3933.

Zetterstrom, et al., "Dopamine Neuron Agenesis in Nurr1-Deficient Mice", Science, vol. 276, Apr. 11, 1997, pp. 248-450.

Jeong, et al., "Orphan Nuclear Receptor NUR77 Translocates to Mitochondria in the Early Phase of Apoptosis Induced by Synthetic Chenodeoxycholic Acid Derivatives in Human Stomach Cancer Cell Line SNU-1", Ann. N.Y. Acad. Sci. 1010: 171-177(2003).

* cited by examiner

```
   1 ATGCCCTGTA TCCAAGCCCA ATATGGGACA CCAGCACCAA GCCCAGGACC CCGAGACCAC CTGGCAAGCG ACCCCCTGAC CCCCGAGCTC AGCAAGCCCA
 101 CCATGGACCT GGCCAGCCCT GAGGCAGCCC CCACCGCCCC CCAGCCCCTG CACGGCCCTG GCACTTTCAT GGACGGCTAC ACGGGGGAGT TTGACACCTT
 201 CCTGTACCAG CTGCCGGGAA CGGCCCAGCC ATGCTCTTCG GCCTCCTCTC CGGCCTCCTC CACGTCCTCC TCCTCGGCCA CCTCCCCCGC CCTCTGCTTCC
 301 TTCAAGTTTG AGGACTTCCA GGTGTACGGC TGCTACCCTG GCCGTCCCTG GCCCCTGAGG GACGAGACCC TGTCCTCCAG CGGTTCCGAC TACTACGGCA
 401 GCCCCTGCTC AGCGCCGTCC CCGTCCACGC CCAGCTTCCA GCCAACCCCCAG GCCAGTGGCT GTTCGGCCCC TTCTCACCCA GCCAGACGTA
 501 CGAAGGCCTG CGGGCATGGA CAGAGCAACT GCCCAAGGCT TCTGGGCACC CCCTTCAGCC TGCCTTTTTT TCCTTCAGCC CCCCTACTGG TCCCAGTCCC
 601 AGCCTTGCCC AGAGCCCCTT GAAGCTGTTC CCCTCACAGG CCACCTGCCA GCTGGGGGAG AGAGAAAAGT ATTCCATATC CACGGCTTTC CCGGGCCTGG
 701 CGGCCACTTC TCCACACCTC GACGGCCCAG CGCACCGGTG CCTTCGGCCA AGGCCCGGAG CGGGCCCCC AGTGGAAGCG AGGGCCGCTG
 801 TGCCGTGTGT GGGGACAACG CTTCGTGCCA GCATTACGGC GTCCGCACCT GCGAGGGCTG TAAGGGCTTC TTCAAGGCA CAGTACAGAA AAACGCCAAG
 901 TACATCTGCC TGGCTAACAA GGACTGCCCT GTGGACAAGA GGCGGCGAAA CCGCTGCCAG CCGCTGTCGCT TCCAGAAGTG CCTGGCCGTA GGCATGGTGA
1001 AGGAAGTTGT CCGGACAGAC AGCCTGAAGG GGCGGCGGGG TCGGCTCCCT TCGAAGCCCA AGCAGCCCCC GGACGCCTCC CCTGCCAACC TCCTCACGTC
1101 CCTGGTCAGG GCACACCTGG ACTCCGGGCC CAGCACAGCC AAACTGGACT ACTCCAAGTT CCAGGAGCTG GTACTGCCCC ACTTCGGGAA GGAAGATGCC
1201 GGGACGTGC AGCAGTTCTA CGACCTGCTT TCGGGTTCCC TGGAGGTCAT CCGCAAGTGG GCCGAGAAGA TCCCCGGCTT TGCCGAGCTG TCCCCGGGTG
1301 ACCAGGACCT GCTGCTGGAG TCGGCCTTCC TGGAGCTCTT CATCCTCCGC GTCGCCTACC GCTCGAAGCC GGCCGAGGGG AAGCTCATCT TCTGCTCGGG
1401 CCTGGTGCTC CACCGGCTGC AGTGCGCCCG CGGCTTTGGC GACTGGATCG ACAGCATTCT GGCCTTCTCT CGGTCCCTGC ACGGCCTGGT GGTGGACGTC
1501 CCTGCCTTCG CCTGCCTCTC GGCGGCCCAT GGCGGCTCGT CTCATCACAG CCGGCACACGG GCTGCAAGAG CCAAGGCGGG TGGAGGAGCT GCAAAATCGC ATCGCCAGCT
1601 GCCTGAAGGA GCACGTCTCG GCGTGGCGG GCGAACCGCA GCCGGCCAGC TGCCTGCTGG GCCTGCTGGG CAAGCTCCCC GAGCTGCGGA CCCTGTGCAC
1701 CCAGGGCTTG CAACGCATCT TCTACCTCAA GCTGGAGGAC CTGGTGCCCC CTCCGGCCAT TGTCGACAAG ATCTTTATGG ACACGCTGCC CTTCTGA
```

FIG. 1

```
  1 MPCIQAQYGT PAPSPGPRDH LASDPLTPEL SKPTMDLASP EAAPTAPTAL
 51 PSFSTFMDGY TGEFDTFLYQ LPGTAQPCSS ASSSASSTSS SSATSPASAS
101 FKFEDFQVYG CYPGPLSGPL DETLSSSGSD YYGSPCSAPS PSTPSFQPPQ
151 LSPWDGSFGP FSPSQTYEGL RAWTEQLPKA SGHPQPPAFF SFSPPTGPSP
201 SLAQSPLKLF PSQATCQLGE GESYSISTAF PGLAPTSPHL DGPGMLDAPV
251 TSTKARSGAP SGSEGRCAVC GDNASCQHYG VRTCEGCKGF FKRTVQKNAK
301 YICLANKDCP VDKRRRNRCQ FCRFQKCLAV GMVKEVVRTD SLKGRRGRLP
351 SKPKQPPDAS PANLLTSLVR AHLDSGPSTA KLDYSKFQEL VLPHFGKEDA
401 GDVQQFYDLL SGSLEVIRKW AEKIPGFAEL SPGDQDLLLE SAFLELFILR
451 LAYRSKPAEG KLIFCSGLVL HRLQCARGFG PRRVEELQNR IASCLKEHVS AVAGEPQPAS
501 PAFACLSALV LITDRHGLQE PRRVEELQNR IASCLKEHVS AVAGEPQPAS
551 CLSRLLGKLP ELRTLCTQGL QRIFYLKLED LVPPPPIVDK IFMDTLPF 598*
```

FIG.2

```
RhNur77:   1   MPCIQAQYGTPAPSPGPRDHLASDPLTPELSKPTMDLASPEAAPTAPTALPSFSTFMDGY  60
               MPCIQAQYGTPAPSPGPRDHLASDPLTPE  KPTMDLASPEAAP APTALPSFSTFMDGY
huNur77:   1   MPCIQAQYGTPAPSPGPRDHLASDPLTPEFIKPTMDLASPEAAPAAPTALPSFSTFMDGY  60

RhNur77:  61   TGEFDTFLYQLPGTAQPCSSASSSASSTSSSSATSPASASFKFEDFQVYGCYPGPLSGPL 120
               TGEFDTFLYQLPGT QPCSSASSSASSTSSSSATSPASASFKFEDFQVYGCYPGPLSGP+
huNur77:  61   TGEFDTFLYQLPGTVQPCSSASSSASSTSSSSATSPASASFKFEDFQVYGCYPGPLSGPV 120

RhNur77: 121   DETLSSSGSDYYGSPCSAPSPSTPSFQPPQLSPWDGSFGPFSPSQTYEGLRAWTEQLPKA 180
               DE LSSSGSDYYGSPCSAPSPSTPSFQPPQLSPWDGSFG  FSPSQTYEGLRAWTEQLPKA
huNur77: 121   DEALSSSGSDYYGSPCSAPSPSTPSFQPPQLSPWDGSFGHFSPSQTYEGLRAWTEQLPKA 180

RhNur77: 181   SGHPQPPAFFSFSPPTGPSPSLAQSPLKLFPSQATCQLGEGESYSISTAFPGLAPTSPHL 240
               SG PQPPAFFSFSPPTGPSPSLAQSPLKLFPSQAT QLGEGESYS+ TAFPGLAPTSPHL
huNur77: 181   SGPPQPPAFFSFSPPTGPSPSLAQSPLKLFPSQATHQLGEGESYSMPTAFPGLAPTSPHL 240

RhNur77: 241   DGPGMLDAPVTSTKARSGAPSGSEGRCAVCGDNASCQHYGVRTCEGCKGFFKRTVQKNAK 300
               +G G+LD PVTSTKARSGAP GSEGRCAVCGDNASCQHYGVRTCEGCKGFFKRTVQKNAK
huNur77: 241   EGSGILDTPVTSTKARSGAPGGSEGRCAVCGDNASCQHYGVRTCEGCKGFFKRTVQKNAK 300
```

FIG. 3A

```
RhNur77: 301 YICLANKDCPVDKRRRNRCQFCRFQKCLAVGMVKEVVRTDSLKGRRGRLPSKPKQPPDAS 360
              YICLANKDCPVDKRRRNRCQFCRFQKCLAVGMVKEVVRTDSLKGRRGRLPSKPKQPPDAS
huNur77: 301 YICLANKDCPVDKRRRNRCQFCRFQKCLAVGMVKEVVRTDSLKGRRGRLPSKPKQPPDAS 360

RhNur77: 361 PANLLTSLVRAHLDSGPSTAKLDYSKFQELVLPHFGKEDAGDVQQFYDLLSGSLEVIRKW 420
              PANLLTSLVRAHLDSGPSTAKLDYSKFQELVLPHFGKEDAGDVQQFYDLLSGSLEVIRKW
huNur77: 361 PANLLTSLVRAHLDSGPSTAKLDYSKFQELVLPHFGKEDAGDVQQFYDLLSGSLEVIRKW 420

RhNur77: 421 AEKIPGFAELSPGDQDLLLESAFLELFILRLAYRSKPAEGKLIFCSGLVLHRLQCARGFG 480
              AEKIPGFAELSP DQDLLLESAFLELFILRLAYRSKP  EGKLIFCSGLVLHRLQCARGFG
huNur77: 421 AEKIPGFAELSPADQDLLLESAFLELFILRLAYRSKPGEGKLIFCSGLVLHRLQCARGFG 480

RhNur77: 481 DWIDSILAFSRSRLHSLVVDVPAFACLSALVLITDRHGLQEPRRVEELQNRIASCLKEHVS 540
              DWIDSILAFSRSRLHSL+VDVPAFACLSALVLITDRHGLQEPRRVEELQNRIASCLKEHV+
huNur77: 481 DWIDSILAFSRSRLHSLLVDVPAFACLSALVLITDRHGLQEPRRVEELQNRIASCLKEHVA 540

RhNur77: 541 AVAGEPQPASCLSRLLGKLPELRTLCTQGLQRIFYLKLEDLVPPPIVDKIFMDTLPF 598
              AVAGEPQPASCLSRLLGKLPELRTLCTQGLQRIFYLKLEDLVPPPI+DKIFMDTLPF
huNur77: 541 AVAGEPQPASCLSRLLGKLPELRTLCTQGLQRIFYLKLEDLVPPPIIDKIFMDTLPF 598
```

FIG. 3B

```
RhNur77:   1  atgccctgtatccaagcccaatatgggacaccagcccagacccccgagaccac  60
              ||||||||||||||||||||||||||||||||||||||||||||||||||||
HuNur77:   1  atgccctgtatccaagcccaatatgggacaccagcaccagtccggacccgtgaccac  60

RhNur77:  61  ctggcaagcgacccctgacccccgagctcagcaagcccaccatgacctggcagccct  120
              ||||||||||||||||||||||||||||||||||||||||||||||||||||
HuNur77:  61  ctggcaagcgacccctgacccctgagttcatcaagcccaccatgacctggcagcccc  120

RhNur77: 121  gaggcagcccccacgcccccacggccctgccagcttcagcactttcatggacggctac  180
              ||||||||||||||||||||||||||||||||||||||||||||||||||||
HuNur77: 121  gaggcagcccccgtgccccactgccctgccagcttcagcaccttcatggacggctac  180

RhNur77: 181  acggggagtttgacaccttcctgtaccagctgccgggaacggccagcatgctcttcg  240
              ||||||||||||||||||||||||||||||||||||||||||||||||||||
HuNur77: 181  acagagagtttgacaccttcctctaccagctgccaggaacagtccagcatgctcctca  240

RhNur77: 241  gcctcctcttcggcctcctccagcgtcctcctcggccacctcccccgctctgcttcc  300
              ||||||||||||||||||||||||||||||||||||||||||||||||||||
HuNur77: 241  gcctcctcctcggcctcctccagcgtcctccacatcctcgtcctcagccacctcccctgcttcc  300

RhNur77: 301  ttcaagtttgagggacttccagtgtacggctgctacctgagcggtccctg  360
              ||||||||||||||||||||||||||||||||||||||||||||||||||||
HuNur77: 301  ttcaagttcgagggacttccagtgtacggctgctacctgagcgccagtg  360

RhNur77: 361  gacgagaccctgtcctccagcggttccgactactacggcagccctgctcagcgccgtcc  420
              ||||||||||||||||||||||||||||||||||||||||||||||||||||
HuNur77: 361  gatgaggccctgtcctccagtgtctgactactatggcagcccctgctcggcccgtcg  420
```

FIG.4A

```
RhNur77: 421  ccgtccacgcccagcttccagccaccccagctctctccctgggatggctcgttcggcccc 480
              ||| ||||||||||||||||||||||||||||||||||||||||||||||||||||||||
HuNur77: 421  ccctccacgcccagcttccagccgccccagctctctccctgggatggctccttcggccac 480

RhNur77: 481  ttctcaccagccagacgtacgaaggctgcgggcatggacagagcaactgcccaaggct 540
              |||||| ||||||||||| ||||||||||||||||||||||||||| ||||||| ||
HuNur77: 481  ttctcgccagccagacttacgaaggctgcgggcatggacagagcagagcgcccaagcc 540

RhNur77: 541  tctgggcaccccccagccgcctgccttttttccttcagccctctactggtcccagtccc 600
              |||||| |||||||||||||||||||||| ||||||||||| ||||||||||||||||
HuNur77: 541  tctgggcccccccagccgcctgccttttttccttcagtcctcccccaccggccccagccc 600

RhNur77: 601  agccttgcccagagcccctgaagtcgttccccacaggccacctgccagctggggag 660
              ||||| ||||||||||||||| |||||||||||||||||| ||||||||||||||||||
HuNur77: 601  agcctggcccagagcccctgaagttgttccccacaggccaccaccagctggggag 660

RhNur77: 661  agagaaagttattccatatccacggctttcccggcctgcgccacttctccacacctc 720
              |||| ||||| || |||| ||||||||||||| |||| ||| ||||||||||||||
HuNur77: 661  ggagagagctattccatgcctacggccttcccaggtttggcacccactcctccacacctt 720

RhNur77: 721  gacggcccagggatgctggacgcaccgtgcttcggcaaggcccgagcggggcccc 780
              | ||| ||| ||||||| ||| ||| ||| ||||||||||| || ||||||||||
HuNur77: 721  gagggctcggggatactggatacaccgtgacctcaaccaaggcccgagcggggcccca 780
```

FIG.4B

```
RhNur77:  781  agtggaagcgagggccgctgtgccgtgtgtgggacaacgcttcgtgccagcattacggc  840
               |||||||  ||  ||||||||||||||||||| |||||||||||||||||||||||  ||
HuNur77:  781  ggtggaagtgaaggccgctgtgctgtgtgtgggacaacgcttcatgccagcattatggt  840

RhNur77:  841  gtccgcacctgcgagggctgtaagggcttcttcaagcgcacagtacagaaaacgccaag  900
               |||||||| |||||||||||| |||||||||||||||||||||||||||||||||||||
HuNur77:  841  gtccgcacatgtgagggctgcaagggcttcttcaagcgcacagtgcagaaaacgccaag  900

RhNur77:  901  tacatctgcctggctaacaaggactgccctgtgacaagagaggcgaaccgctgccag  960
               ||||||||||||||||||||||||||||||||||||||||||||||||||||||||
HuNur77:  901  tacatctgcctggctaacaaggactgccctgtgacaagagaggcgaaccgctgccag  960

RhNur77:  961  ttctgtcgcttccagaagtgcctggcgtaggcatggtgaaggaagttgtccggacagac  1020
               ||||| ||||||||||||||||||||||||  ||||||||||||||||||||||||| 
HuNur77:  961  ttctgccgcttccagaagtgcctggcgtgggcatggtgaaggaagttgtccgaacagac  1020

RhNur77: 1021  agcctgaaggggcggggtcggctccctctcgaagcccaagcagccccggacgcctcc  1080
               ||||||||||||||||  ||||| ||||| |||||||||||||||||||  ||||||
HuNur77: 1021  agcctgaaggggcggcggggccgcctacccttcaaaacccaagcagccccagatgcctcc  1080

RhNur77: 1081  cctgccaacctcctcacgtccctgttcagggcacacctgactccgggccagcacagcc  1140
               ||||||||  |||||| || ||||||||||||||||| ||||||||||||||||||
HuNur77: 1081  cctgccaatctccctcacttccctgttcgtgcacacctgactccagccagcactgcc  1140

RhNur77: 1141  aaactgactactccaagttccaggagctggtactgccccacttcgggaaggaagatgcc  1200
               |||||||||||||||||||||||||||| ||||| |||||||||||||||||||||
HuNur77: 1141  aaactgactactccaagttccaggagctgctgctgccccacttggggaaggaagatgct  1200
```

FIG.4C

```
RhNur77: 1201 gggacgtgcagcagttctacgacctgctttcgggtcctggagtcatccgcaagtgg 1260
               ||||||||| || |||||||||||||||||||||||| ||||||||||||||||||
HuNur77: 1201 ggggatgtacagcagttctacgacctgctctccggttctctggaggtcatccgcaagtgg 1260

RhNur77: 1261 gccgagaagatccccggctttgccgagctgtccccggtgaccaggacctgctgctggag 1320
               |||||||||||||||||||| ||||||||| |||||||||||||||| ||||||||||
HuNur77: 1261 gcgagaagatccctggctttgctgagctgtcaccggctgaccaggacctgttgctggag 1320

RhNur77: 1321 tcggccttcctggagctcttcatcctccgcttgctcaccgcctgaagccggccgagggg 1380
               ||||||||||||||||||| |||||||||| ||| ||| |||| ||||||||||||||
HuNur77: 1321 tcggccttcctggagctcttcatcctccgcttgggctacaggtctaagccaggcgagggc 1380

RhNur77: 1381 aagctcatcttctgctcggcctggtgctccacgcgctgcagtgcgcccgcggcttggc 1440
               |||||||||||||||||||||||||||||||| ||||| ||||||||| |||| |||
HuNur77: 1381 aagctcatcttctgctcaggcctggtgctacaccggctgcagttgccgtggcttcggg 1440

RhNur77: 1441 gactggatcgacagcattctggcctttctctcggttccctgcacggcctggtggtggacgtc 1500
               |||||||| ||| || ||||||||||| || || ||||||||||||| |||||||||||
HuNur77: 1441 gactggattgacagtatcctggccttttctcaagttccctgcacagcttgcttgtcgatgtc 1500

RhNur77: 1501 cctgccttcgcctgcctgctctcggcctctgtcgtcctcatcacagaccggcacgggctgcaagag 1560
               |||||||| |||||||| || || |||||||| ||||| |||||| |||||| ||||||| |||
HuNur77: 1501 cctgccttgcctgcctctctgcccttgtcctcatcaccgaccgcatgggctgcaggag 1560

RhNur77: 1561 ccaaggcgggtggaggagctgcaaatcgcatgccagctgcctgaaggagcacgtctcg 1620
               |||| ||||||||||||||||||| ||||||||||||||||||||||||||||| |
HuNur77: 1561 ccgcgggtggaggagctgcagaaccgtcagaatcgcagcagctgcctgaaggagcacgtggca 1620
```

FIG.4D

RhNur77: 1621 gccgtgcgggcgaaccgcagccagccggctgtcacgcctgctgggcaagctcccc 1680
              ||  |||||||||| ||  ||||||||||||| ||||| || |||||||||  ||
HuNur77: 1621 gctgtgcgggcgagcccagccagccggctgtcacgtctgttgggcaaactgccc 1680

RhNur77: 1681 gagctgcggacccgtgcaccagggctgcaacgcatcttctacctcaagctggaggac 1740
              |||||||||||||||||||| ||| |||||||||||||||||||||||||||||||
HuNur77: 1681 gagctgcggacccgtgcaccagggcctgcaacgcatcttctacctcaagctggaggac 1740

RhNur77: 1741 ttggtgccccctccgcgccattgtcgacaagatctttatggacacgctgccccttctga 1797
              |||||||| |||||| || |||| ||||||||||||| |||||||||||||||||||||
HuNur77: 1741 ttggtgcccctccaccatcattgacaagatctttcatgacacgctgcccttctga 1797

FIG.4E

RHESUS MONKEY NUR77

CROSS REFERENCE TO RELATED APPLICATIONS

This application claims the benefit of U.S. Provisional Application No. 60/662,197, filed Mar. 16, 2005, the contents of which are incorporated herein by reference in their entirety.

BACKGROUND OF THE INVENTION (1) Field of the Invention

The present invention relates to the *Macaca mulatta* (rhesus monkey) Nur77 (rhNur77) nuclear receptor and the nucleic acid encoding the rhNur77 nuclear receptor. The present invention further relates to methods for identifying analytes that modulate expression or activity of Nur77. Analytes that affect Nur77 expression or activity may be useful for treating or inhibiting inflammatory diseases such as osteoarthritis and various bone, neurological, and prostrate disorders. The rhNur77 may also be useful in treatments for particular cancers such as lung cancer, prostrate cancer, colon cancer, ovarian cancer, or gastric cancer.

(2) Description of Related Art

Nur77 is a transcription factor that belongs to the superfamily of nuclear receptors, which includes receptors for various steroid hormones, retinoids, thyroid hormone, and estradiol. The superfamily further includes a large group of receptors classified as orphan receptors because their natural ligands are not yet known. Nur77 is currently classified as an orphan receptor and has been variously known as HMR, N10, TR3, NP10, GFRP1, NAK-1, NGFIB, or MGC9485. Nur77 is expressed in various peripheral tissues and in some regions of the brain and has been implicated to have a role in cell proliferation, differentiation, and apoptosis.

Nur77 exhibits a close structural relationship to the orphan receptors Nurr1 (Hazel et al., Proc. Natl. Acad. Sci. USA. 85: 8444-8448 (1988); Milbrant, Neuron 1: 183-188 (1998); Ryseck et al., EMBO J. 8: 3327-3335 (1989); Nakai et al., Mol. Endocrinol. 4: 1438-1443 (1990)) and NOR-1 (Ohkura et al., Biochem. Biophys. Res. Comm. 205: 1959-1965 (1994); Maruyama et al., Cancer Lett. 96:117-122 (1995); Hedvat and Irving, Mol. Endocrinol. 9: 1692-1700 (1995)). All three of these orphan nuclear receptors comprise the Nurr subfamily of nuclear receptors which has been characterized as being able to bind to the same cis-acting consensus nucleotide sequence—the NGFI-B response element (NBRE)—to regulate target gene expression (Ohkura et al., Biochem. Biophys. Res. Comm. 205: 1959-1965 (1994); Wilson et al., Science 252: 1296-1300 (1991); Wilson et al., Mol. Cell Biol. 13: 5794-5804 (1993); Murphy et al., Gene Express. 5: 169-179 (1995)). For example, Nurr1 and Nur77 regulate expression of the Corticotropin Releasing Hormone (CRH) and proopiomelanocortin (POMC) genes by interacting with specific cis-acting sequences in their proximal promoter region.

Like most nuclear receptors of the nuclear receptor superfamily, Nur77 consists of an amino-terminal transactivation function 1 (AF1) near the amino terminus, which enables ligand-independent transcription activation; a core DNA binding domain (DBD) located near the center of the protein, which contains two highly conserved zinc finger motifs and which binds to specific nucleotide sequences; a hinge region, which permits protein flexibility to allow for simultaneous receptor dimerization and DNA binding; a conserved ligand binding domain (LBD) near the carboxy terminus, which includes a dimerization interface; and, a carboxyl-terminal activation function 2 (AF2) near the carboxy terminus, which enables ligand-independent transcription activation. Many nuclear receptors act as dimers, either as homodimers or as heterodimers. The dimerization interface in the LBD, the I-box, has been mapped to a region in the carboxyl terminal part of the LBD that corresponds to helix 10 in the canonical nuclear receptor LBD structure (Perlmann et al., Mol. Endocrinol. 10: 958-966 (1996); Lee et al. Mol. Endocrinol. 12: 325-332 (1998)).

Unlike most nuclear receptors, the Nurr subfamily of nuclear receptors are encoded by immediate early genes whose expression can be differentially induced in response to a variety of extracellular stimuli such as growth factors (Hazel et al., ibid.; Milbrandt, ibid.), neurotransmitters (Watson and Milbrandt, Mol. Cell. Biol. 9: 4213-4219 (1989)), and polypeptide hormones (Wilson et al., Mol. Cell. Biol. 13: 861-868 (1993); Murphy and Conneely, ibid.; Davis and Lau, Mol. Cell Biol. 14: 3469-3483 (1994)). Nurr1 and Nur77 are rapidly induced by CRH in primary pituitary cells, resulting in increased synthesis of POMC (Murphy and Conneely, ibid.). Glucocorticoid repression of the POMC gene is mediated by glucocorticoid receptor dependent inhibition of activation of the POMC gene by Nurr1 and Nur77 (Evans, ibid.; Philips et al., Mol. Cell. Biol. 17: 5952-5959 (1997)) and appears to antagonize negative feedback of ACTH synthesis and secretion by glucocorticoid in pituitary corticotrope cells (Okabe et al., J. Endocrinol. 156: 169-175 (1998). Because NOR-1 possesses an identical DNA binding domain and is capable of binding the same cis-acting consensus sequence as Nurr1 and Nur77, it has been included in the Nurr subfamily. Therefore, the close structural relationship, the identical cis-acting consensus sequence, and the ability of the different members of the Nurr subfamily of transcription factors to functionally complement one another are strong indications that the Nurr subfamily members might have redundancy of function.

Nur77 forms heterodimers with retinoid X receptor (RXR) (Perlmann and Jansson, Genes Dev. 9: 769-782 (1995); Forman et al. (1995); Zetterstrom et al., Science 276: 248-250 (1996)). The unique ability of the Nur77/RXR heterodimer complex to transduce RXR signals establishes a novel response pathway. Heterodimer formation may impart allosteric changes upon the LBD of the Nur77. These allosteric changes may confer transcriptional activities onto the Nur77-RXR heterodimer that are distinct from those of the Nur77 or RXR monomers. This would permit a limited number of regulatory proteins to generate a diverse set of transcriptional responses to multiple hormonal signals.

Nur77 appears to have a role in both apoptosis and cell proliferation. Kolluri et al. (Molec. Cell. Biol. 23: 8651-8667 (2003)), and Wilson et al. (Cancer Res. 63: 5401-5407 (2003)) have shown that Nur77 can induce apoptosis or cellular differentiation in the same cells depending on the stimuli and its cellular location. Cao et al. (Molec. Cell. Biol. 24: 9705-9725 (2004) has shown that RXR regulates Nur77/thyroid hormone receptor 3-dependent apoptosis by modulating its nuclear export and translocation to the mitochondria where it induces apoptosis. Other researchers have shown that parathyroid hormone can regulate Nur77 expression in bone (Tetradis et al., in Biochem. Biophys. Res. Comm. 281: 913-916 (2001)) and LH can regulate Nur77 expression in testicular Leydig cells (Song et al., Endocrinol. 142: 5116-5123 (2001). Promyelocytic leukemia protein PML is a tumor and growth suppresser that inhibits Nur77-mediated transcription by interacting with the DNA-binding domain of Nur77, which prevents it from binding its target promoter (Wu et al., oncogene 21: 3925-3933 (2002). The role of Nur77 in signal transduction has been discussed by Winoto and Littman, Cell 109: S57-S66 (2002).

BRIEF SUMMARY OF THE INVENTION

The present invention provides the *Macaca mulatta* (rhesus monkey) Nur77 nuclear receptor (rhNur77) and the nucleic acid encoding the rhNur77. The present invention further provides methods for identifying analytes that modulate expression or activity of Nur77. Analytes that affect Nur77 expression or activity may be useful for treating or inhibiting inflammatory diseases such as osteoarthritis and various bone, neurological, and prostrate disorders. The rhNur77 may also be useful in treatments for particular cancers such as lung cancer, prostate cancer, colon cancer, ovarian cancer, and gastric cancer.

Therefore, the present invention provides an isolated nucleic acid molecule comprising a nucleotide sequence encoding an rhNur77 polypeptide or fragment thereof having the amino acid sequence shown in SEQ ID NO:2 or fragment or subsequence thereof. In a further aspect of the invention, the nucleic acid molecule encoding the rhNur77 comprises the nucleotide sequence of SEQ ID NO:1 or fragment or subsequence thereof. The present invention further provides an isolated nucleic acid encoding the LBD or the DBD of the rhNur77 polypeptide. For example, the present invention provides a nucleic acid encoding the LBD, which comprises the nucleotides from about 997 to about 1698 of SEQ ID NO:1, and a nucleic acid encoding the DBD, which comprises the nucleotides from about 800 to about 996 of SEQ ID NO:1. The present invention further includes nucleic acids comprising SEQ ID NO:1 wherein nucleotide 1435 is a cytosine.

The present invention further provides an isolated polypeptides comprising an amino acid sequence of SEQ ID NO:2. In particular, the present invention provides a polypeptide comprising amino acids 1 to 598 of SEQ ID NO:2, and fragments thereof, for example; a polypeptide comprising the LBD, preferably, amino acids from about 332 to about 566 of SEQ ID NO:2; or, a polypeptide comprising the DBD, preferably amino acids from about 265 to about 332 of SEQ ID NO:2. The present invention further includes polypeptides comprising SEQ ID NO:2 wherein amino acid 479 is a leucine.

The present invention further provides an antibody which binds a polypeptide comprising an amino acid sequence of SEQ ID NO:2. In further aspects, the antibody is a polyclonal antibody or a monoclonal antibody.

The present invention further still provides a vector comprising a nucleic acid encoding an rhNur77 polypeptide or fragment thereof which comprises an amino acid sequence of SEQ ID NO:2. Preferably, the nucleic acid encoding the rhNur77 comprises the sequence of SEQ ID NO:1 or fragment or subsequence thereof. In particular aspects of the vector, the vector comprises a nucleic acid encoding the LBD or the DBD of the rhNur77. In further aspects of the above vector, the nucleic acid encodes a fusion or chimeric protein, which comprises the rhNur77 polypeptide, the LBD of the rhNur77, or the DBD of the Nur77 fused to a heterologous protein. In particular aspects of the vector, the fusion protein comprises the rhNur77 LBD fused to the GAL4 yeast transcription activation factor DBD or glucocorticoid receptor (GR) DBD; or, the H1 alpha helix of the Nur77 LBD fused to the GAL4 or GR LBD and the remainder of the Nur77 LBD fused to the herpesvirus VP16 activation domain. In a further still aspect of the above vector, the present invention further provides a vector wherein the nucleic acid encoding the rhNur77 polypeptide or fragment thereof, or fusion protein, is operably linked to a heterologous promoter. The heterologous promoter can be a constitutive promoter or an inducible promoter.

The present invention further still provides a cell comprising a nucleic acid encoding an rhNur77 polypeptide or fragment thereof having an amino acid sequence of SEQ ID NO:2 wherein the nucleic acid is operably linked to a heterologous constitutive or inducible promoter which enables expression of the rhNur77 or fragment thereof in the cell. Preferably, the nucleic acid comprises the sequence of SEQ ID NO:1 or a fragment or subsequence thereof. For example, the nucleic acid can comprise nucleotides from about 997 to about 1698 of SEQ ID NO:1 (wherein nucleotide 1435 is a thymidine or cytosine), which encode the rhNur77 LBD, or nucleotides from about 800 to about 996 of SEQ ID NO:1, which encode the rhNur77 DBD.

In a further aspect of the above cell, the nucleic acid encodes a fusion or chimeric protein comprising the rhNur77 polypeptide, the Nur77 LBD or the Nur77 DBD fused to a heterologous protein. In particular aspects of the above cell, the fusion protein comprises the rhNur77 LBD fused to the GAL4 yeast transcription activation factor DBD or GR DBD; or, the H1 alpha helix of the LBD fused to the GAL4 or GR LBD and the remainder of the LBD fused to the herpesvirus VP16 activation domain. In a further still aspect of the above cell, the present invention provides a vector wherein the nucleic acid encoding the rhNur77 polypeptide or fragment thereof, or fusion protein, is operably linked to a heterologous constitutive or inducible promoter.

In a further aspect of the above cell, the cell further includes a second nucleic acid encoding a reporter gene, which encodes an assayable product, wherein the nucleic acid encoding the reporter gene is operably linked to a promoter responsive to the rhNur77. In further aspects of the above cell, the rhNur77 responsive promoter comprises one or more copies of a Nur77 responsive sequence, for example, an NGFI-B (Nur77)-responsive element (NBRE), a Nur77 response element (NurRE) or an RA response element (βRARE) in the RARβ promoter. Examples of Nur77 responsive promoters include the promoter for the gene encoding NGFI-B protein, the gene encoding the pro-opiomelanocortin (POMC), or the gene encoding the retinoid acid receptor (RAR), or a minimal promoter such as the CMVie or HSV TK promoter operably linked to one or more copies of a Nur77 responsive sequences.

In a further still aspect of the above cell, the cell expresses an endogenous retinoid X receptor (RXR) or includes a third nucleic acid which encodes the RXR for ectopic expression of the RXR.

The present invention further still provides a method for producing an rhNur77 polypeptide or fragment thereof comprising (a) providing a nucleic acid encoding the rhNur77 polypeptide operably linked to a heterologous promoter; (b) introducing the nucleic acid into a cell to produce a recombinant cell; and (c) culturing the recombinant cell under conditions suitable for expression of the nucleic acid encoding the rhNur77 to produce the rhNur77 polypeptide or fragment thereof. Preferably, the nucleic acid comprises the nucleotide sequence of SEQ ID NO:1 or subsequence thereof. For example, a nucleic acid fragment is provided which encodes the rhNur77 LBD comprising amino acids from about 333 to about 598 of SEQ ID NO:2 or comprising nucleotides from about 997 to about 1698 of SEQ ID NO:1 or the DBD comprising amino acids from 265 to 332 of SEQ ID NO:2 or comprising nucleotides from about 800 to about 996 of SEQ ID NO:1.

In further aspects of the above method, the nucleic acid encodes a fusion or chimeric protein comprising the Nur77 polypeptide, the LBD or the DBD fused to a heterologous protein. In particular aspects of the above method, the fusion protein comprises the rhNur77 LBD fused to the GAL4 yeast transcription activation factor DBD or GR DBD; or, the H1 helix of the LBD fused to the GAL4 or GR LBD and the remainder of the LBD fused to the herpesvirus VP16 activation domain. In further still aspects of the above methods, the present invention further provides a vector wherein the nucleic acid encoding the rhNur77 polypeptide or fragment thereof, or fusion protein, is operably linked to a heterologous promoter. In further still aspects of the above method, the cell is a selected from the group consisting of mammalian cells, prokaryote cells, insect cells, fungal cells, and plant cells. In particular aspects of the above method, the recombinant cell is either transiently transfected with the nucleic acid or is stably transfected cell with the nucleic acid.

The present invention further still provides a method for identifying an analyte that modulates activity of an rhNur77, which comprises (a) providing a recombinant cell that expresses the rhNur77; (b) incubating the recombinant cell in a medium which includes the analyte; and (c) measuring activity of the rhNur77, wherein a change in the activity of the rhNur77 in the presence of the analyte indicates the analyte modulates the activity of the rhNur77. Preferably, the rhNur77 comprises the amino acid sequence of SEQ ID NO:2 or is encoded by a nucleic acid which comprises the nucleotide sequence of SEQ ID NO:1.

In further aspects of the above method, the recombinant cell is a selected from the group consisting of mammalian cells, prokaryote cells, insect cells, fungal cells, and plant cells. In particular aspects of the above method, the recombinant cell is a mammalian cell which is either transiently or stably transfected with a nucleic acid encoding the rhNur77. Preferably, the rhNur77 comprises the amino acid sequence of SEQ ID NO:2 or is encoded by a nucleic acid comprising the nucleotide sequence of SEQ ID NO:1. In a further aspect of the above method, the activity of the rhNur77 is determined by measuring expression of a reporter gene operably linked to a promoter which is responsive to rhNur77. In particular aspects of the above method, the rhNur77 responsive promoter comprises one or more copies of a Nur77 responsive sequence, for example, an NGFI-B (Nur77)-responsive element (NBRE), a Nur77 response element (NurRE) or an RA response element (βRARE) in the RARβ promoter. Examples of Nur77 responsive promoters include the promoter for the gene encoding NGFI-B protein, the gene encoding the pro-opiomelanocortin (POMC), or the gene encoding the retinoid acid receptor (RAR), or a minimal promoter such as the CMVie or HSV TK promoter operably linked to one or more copies of a Nur77 responsive sequences. In further aspects of the above method, the reporter gene encodes luciferase or SEAP.

The present invention further provides a method for identifying an analyte that modulates activity of an rhNur77, which comprises (a) providing a recombinant cell which expresses the rhNur77 and an assayable reporter gene product wherein the reporter gene encoding the product is operably linked to a promoter responsive to the rhNur77; (b) incubating the recombinant cell in a medium which includes an analyte; and (c) measuring the expression of the reporter gene product wherein an increase or decrease of expression of the reporter gene compared to expression in a recombinant cell in the absence of the analyte identifies the analyte that modulates activity of the rhNur77. Preferably, the rhNur77 comprises the amino acid sequence of SEQ ID NO:2 or is encoded by a nucleic acid which comprises the nucleotide sequence of SEQ ID NO:1.

In particular aspects of the above method, the recombinant cell further expresses a retinoid X receptor (RXR). The expression of the RXR can be ectopic or endogenous. In further still aspects, the activity of the rhNur77 is determined by measuring expression of a reporter gene encoding an assayable product which is operably linked to a promoter that is responsive to rhNur77, e.g., a promoter which includes at least one RA response element (βRARE) binding site. In further aspects of the above method, the reporter gene encodes luciferase or SEAP. In particular aspects of the above method, the recombinant cell is a mammalian cell either transiently or stably transfected with nucleic acids encoding the rhNur77 and reporter gene.

The present invention further still provides a method for identifying an analyte that modulates heterodimerization between an rhNur77 and an RXR, which comprises (a) providing a recombinant cell which expresses the rhNur77 and an assayable reporter gene product wherein the reporter gene encoding the product is operably linked to a promoter responsive to the rhNur77/RXR heterodimer; (b) incubating the recombinant cell in a medium which includes an analyte; and (c) measuring the expression of the reporter gene product wherein an increase or decrease of expression of the reporter gene compared to expression in a recombinant cell in the absence of the analyte identifies the analyte that modulates the heterodimerization between the rhNur77 and the RXR. Preferably, the rhNur77 comprises the amino acid sequence of SEQ ID NO:2 or is encoded by a nucleic acid which comprises the nucleotide sequence of SEQ ID NO:1.

In particular aspects of the above method, the RXR expression is endogenous to the cell and in other aspects, the expression is ectopic. In further aspects of the above method, the reporter gene encodes luciferase or SEAP. In particular aspects of the above method, the recombinant cell is a mammalian cell either transiently or stably transfected with nucleic acids encoding the rhNur77 and reporter gene. In further still aspects, the activity of the rhNur77 is determined by measuring expression of a reporter gene encoding an assayable product which is operably linked to a promoter that is responsive to rhNur77, e.g., a promoter which includes at least one RA response element (βRARE) binding site.

In any one of the above methods, the rhNur77 can be provided as a fusion or chimeric protein comprising the LBD of the rhNur77 (amino acids from about 332 to about 598 of SEQ ID NO:2 or encoded by nucleotides from about 997 to about 1698 of SEQ ID NO:1) fused to a heterologous protein. In particular aspects of the above methods, the fusion protein comprises the rhNur77 LBD fused to the GAL4 yeast transcription activation factor DBD or GR DBD.

As used throughout the specification and appended claims, the following definitions and abbreviations apply.

The term "rhNur77" means that the rhNur77 is of *Macaca mulatta* (rhesus monkey) origin, either isolated from rhesus monkey tissue, produced from a nucleic acid obtained from the rhesus monkey by recombinant means, produced from a nucleic acid synthesized in vitro but which encodes the rhNur77, or synthesized in vitro. The term further includes biologically active fragments or portions of the rhNur77, including fusion or chimeric proteins.

The term "Nur77" means that the Nur77 is not of rhesus monkey origin. The Nur77 can be from another organism, for example, a mammal such as rat and mouse, and humans. The Nur77 can either be isolated from tissue of the organism, produced from a nucleic acid obtained from the organism by recombinant means, produced from a nucleic acid synthesized in vitro but which encodes the Nur77, or synthesized in vitro. The term further includes biologically active fragments or portions of the Nur77, including fusion or chimeric proteins. Nur77 has also been referred to TR3 or NGFI-B.

The term "Nur77 binding partner" means a binding partner which can bind rhNur77 or Nur77 regardless of whether it originates from the rhesus monkey, another organism, expressed from a nucleic acid synthesized in vitro, or synthesized in vitro. Examples of Nur77 binding partners include, but are not limited to, retinoid X receptor (RXR), COUP-TF, ligands, co-activators, co-repressors, kinases, transcription factors, membrane proteins, and nucleic acids comprising a Nur77 response element, for example, nucleic acids comprising an NBRE or NurRE binding site. The term further includes biologically active fragments or portions of the Nur77 binding partner.

The term "homologous Nur77 binding partner" means a Nur77 binding partner of rhesus monkey origin. In other words, the Nur77 binding partner is isolated from the rhesus monkey or obtained from recombinant cells expressing the binding partner from DNA encoding the rhesus monkey binding partner.

The term "heterologous Nur77 binding partner" means a Nur77 binding partner not of rhesus monkey origin. For example, the Nur77 binding partner is isolated from a human or obtained from recombinant cells expressing the binding partner from DNA encoding the human binding partner.

The term "promoter" refers to a transcription regulatory sequence or recognition sequence or site on a DNA strand to which RNA polymerase binds. The promoter forms an initiation complex with RNA polymerase to initiate and drive transcriptional activity of a nucleic acid sequence located downstream from the promoter. The promoter can be modified by including activating sequences termed "enhancers" or inhibiting sequences termed "silencers" within the promoter. The term further includes both promoters which are inducible and promoters which are constitutive.

The term "cassette" refers to a nucleotide or gene sequence that is to be expressed from a vector, for example, the nucleotide or gene sequence encoding the rhNur77. In general, a cassette comprises a gene sequence inserted into a vector which in some embodiments provides regulatory sequences for expressing the nucleotide or gene sequence. In other embodiments, the nucleotide or gene sequence provides the regulatory sequences for its expression. In further embodiments, the vector provides some regulatory sequences and the nucleotide or gene sequence provides other regulatory sequences. For example, the vector can provide a promoter for transcribing the nucleotide or gene sequence and the nucleotide or gene sequence provides a transcription termination sequence. The regulatory sequences which can be provided by the vector include, but are not limited to, enhancers, transcription termination sequences, splice acceptor and donor sequences, introns, ribosome binding sequences, and poly(A) addition sequences.

The term "vector" refers to a means by which DNA fragments can be introduced into a host organism or host tissue. There are various types of vectors including plasmid, virus (including adenovirus, herpesvirus, and the like), bacteriophage, and cosmid.

The term "modulator" refers to an agent that upregulates or downregulates (for example, turns on, enhances, inhibits, potentiates, or supplements) or mimics rhNur77 bioactivity in cell type or tissue-selective manner. In one aspect, a modulator can be an analyte that turns on or upregulates activity of rhNur77 from an inactive state to a partially active state or downregulates rhNur77 from an active state partially inactive state. For example, a modulator can be an analyte that when bound to the rhNur77 enables or enhances the binding of the rhNur77 to its binding partner, e.g., a Nur77 responsive promoter, which results in promoter-context selective activities. In another aspect, a modulator can be an analyte that mimics a bioactivity of rhNur77, such as transduction of a signal from a Nur77 binding partner when bound to the binding partner. In a further aspect, an agonist can be an analyte that partially upregulates or downregulates expression of rhNur77. In a further still aspect, a modulator can be an analyte that modulates the expression or activity of a protein, which is located downstream, for example, of a binding partner, thereby mimicking or enhancing the effect of binding of rhNur77 to the binding partner. Full and partial agonists and antagonists are Nur77 are modulators.

The term "agonist" refers to an agent that upregulates (for example, turns on, enhances, potentiates, or supplements) or mimics rhNur77 bioactivity. In one aspect, an agonist can be an analyte that turns on or upregulates activity of rhNur77 from an inactive state to an active state. For example, an agonist can be an analyte that when bound to the rhNur77 enables or enhances the binding of the rhNur77 to its binding partner, e.g., a Nur77 responsive promoter. In another aspect, an agonist can be an analyte that mimics a bioactivity of rhNur77, such as transduction of a signal from a Nur77 binding partner when bound to the binding partner. In a further aspect, an agonist can be an analyte that upregulates expression of rhNur77. In a further still aspect, an agonist can be an analyte that modulates the expression or activity of a protein, which is located downstream, for example, of a binding partner, thereby mimicking or enhancing the effect of binding of rhNur77 to the binding partner.

The term "antagonist" refers to an agent that inhibits, decreases, or suppresses a bioactivity of rhNur77. In one aspect, an antagonist can be an analyte that decreases signaling from rhNur77, for example, an analyte that is capable of binding to rhNur77 or a Nur77 binding partner. A preferred antagonist inhibits or suppresses rhNur77 bioactivity either by interacting with or binding to the rhNur77 or by interacting with or binding to a Nur77 binding partner in a manner that suppresses the interacting or binding of the rhNur77 to the binding partner. In another aspect, an antagonist can be an analyte that downregulates expression of the rhNur77. In a further aspect, an antagonist can also be an analyte that modulates the expression or activity of a protein which is located downstream of the rhNur77, thereby antagonizing the effect of binding of rhNur77 to its binding partner.

A "disorder" is any condition that would benefit from treatment with analytes identified by the methods described herein. This includes chronic and acute disorders or diseases including those pathological conditions which predispose the mammal to the disorder in question.

The term "mammalian" refers to any mammal, including a human being.

The term "treatment" refers to both therapeutic treatment and prophylactic or preventative measures. Those in need of treatment include those already with the disorder as well as those prone to have the disorder or those in which the disorder is to be prevented.

The term "analyte" refers to a compound, chemical, agent, composition, or the like, which can modulate the activity of rhNurr77.

The term "selective androgen receptor modulator" or "SARM" refers to an agent that acts as an agonist in one tissue type while acting as an antagonist or weak or partial agonist in another tissue type. For example, a SARM might act as an antagonists or weak agonist in the prostate but act as a full agonist in the muscle and pituitary.

BRIEF DESCRIPTION OF THE DRAWINGS

FIG. 1 shows the nucleotide sequence for the nucleic acid encoding the rhNur77 (SEQ ID NO:1).

FIG. 2 shows the amino acid sequence for rhNur77 (SEQ ID NO:2).

FIG. 3 shows an amino acid sequence alignment comparison between the amino acid sequence of rhNur77 (SEQ ID NO:2) and the amino acid sequence for the human Nur77 (SEQ ID NO:4). Similar and dissimilar amino acids between the rhNur77 and human Nur77 amino acid sequences are shown. FIG. 3 is shown on two panels as FIG. 3A and FIG. 3B.

FIG. 4 shows a nucleotide sequence alignment comparison between the nucleic acid encoding rhNur77 (SEQ ID NO:1) and a nucleic acid encoding the human Nur77 (SEQ ID NO:3). FIG. 4 is shown on five panels as FIG. 4A, FIG. 4B, FIG. 4C, FIG. 4D, and FIG. 4E.

DETAILED DESCRIPTION OF THE INVENTION

Figure 5:
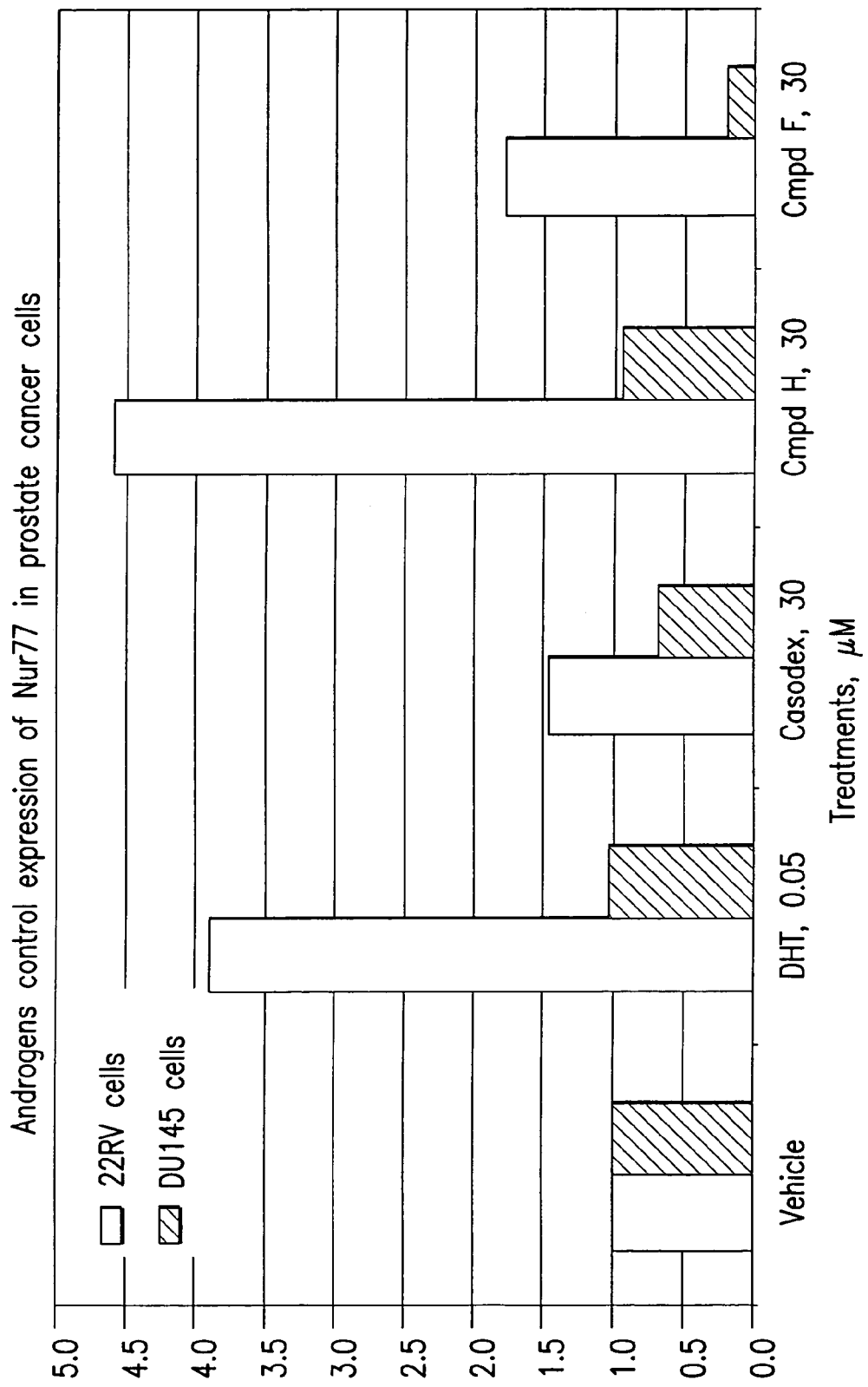
FIG. 5 shows that expression of Nur77 in prostrate cancer cells (22RV1 cells) can be controlled by the androgen dihydrotestosterone (DHT) and various other selective androgen receptor modulators (SARM's). Compounds H and F are SARM's.

The present invention provides the *Macaca mulatta* (rhesus monkey) Nur77 nuclear receptor (rhNur77) and the nucleic acid encoding the rhNur77. The present invention further provides methods or assays for identifying analytes which modulate the molecular or functional interaction between the rhNur77 and one or more homologous or heterologous Nur77 binding partners (for example, a protein binding partner such as retinoid X receptor (RXR) or a nucleic acid binding partner such as a nucleic acid comprising at least one NBRE binding site) and analytes which affect the ability of the rhNur77 or rhNur77/protein binding partner complex to activate transcription at a promoter responsive to the Nur77 or Nur77/protein binding partner complex. Non-limiting examples of methods for identifying such analytes include (i) cell-based assays for identifying analytes which inhibit or suppress the interaction or binding between rhNur77 and one or more homologous or heterologous Nur77 binding partners such as RXR protein expressed in mammalian cells or transcriptional activation of a promoter responsive to Nur77 activation; and (ii) cell-free binding assays for identifying analytes that inhibit or suppress (a) binding between rhNur77 and one or more homologous or heterologous protein binding partners such as RXR protein, (b) binding to a nucleic acid comprising a Nur77 binding site such as the NBRE binding site, or (c) transcriptional activation of a promoter responsive to Nur77 activation. Thus, the methods described herein are useful tools for identifying analytes which modulate molecular and/or functional interactions between Nur77 and one or more homologous or heterologous binding partners or activation of a responsive promoter.

Nur77 appears to have a role in both apoptosis and cell proliferation. Kolluri et al. (Molec. Cell. Biol. 23: 8651-8667 (2003)), and Wilson et al. (Cancer Res. 63: 5401-5407 (2003)) have shown that Nur77 can induce apoptosis or cellular differentiation in the same cells depending on the stimuli and its cellular location. Kolluri et al. show that Nur77 functions in the nucleus to induce cell proliferation and in the mitochondria to induce apoptosis. Kolluri et al. further show that inhibiting DNA binding activity of Nur77 via phosphorylation of the DNA binding domain (DBD) by Jun N-terminal kinase activated by MEKK 1 in lung cancer cells appeared to inhibit Nur77 transcriptional activity and Nur77-induced cell proliferation. Wilson et al. showed that removing the DBD from Nur77 renders prostrate and colon cancer cells apoptotic. Cao et al. (Molec. Cell. Biol. 24: 9705-9725 (2004) has shown that RXR regulates Nur77/thyroid hormone receptor 3-dependent apoptosis by modulating its nuclear export and translocation to the mitochondria where it induces apoptosis. Cao et al., has also shown that induction of apoptosis does not require Nur77's transcriptional activity or DNA binding. Nur77 has also been shown to be induced by various stimuli to target mitochondria in ovarian cancer (Holmes et al., J. Cell Biochem. 89: 262-278 (2003)) and gastric cancer cells (Jeong et al., Ann. N.Y. Acad. Sci. 1010: 171-177 (2003)) as well.

Figure 6:
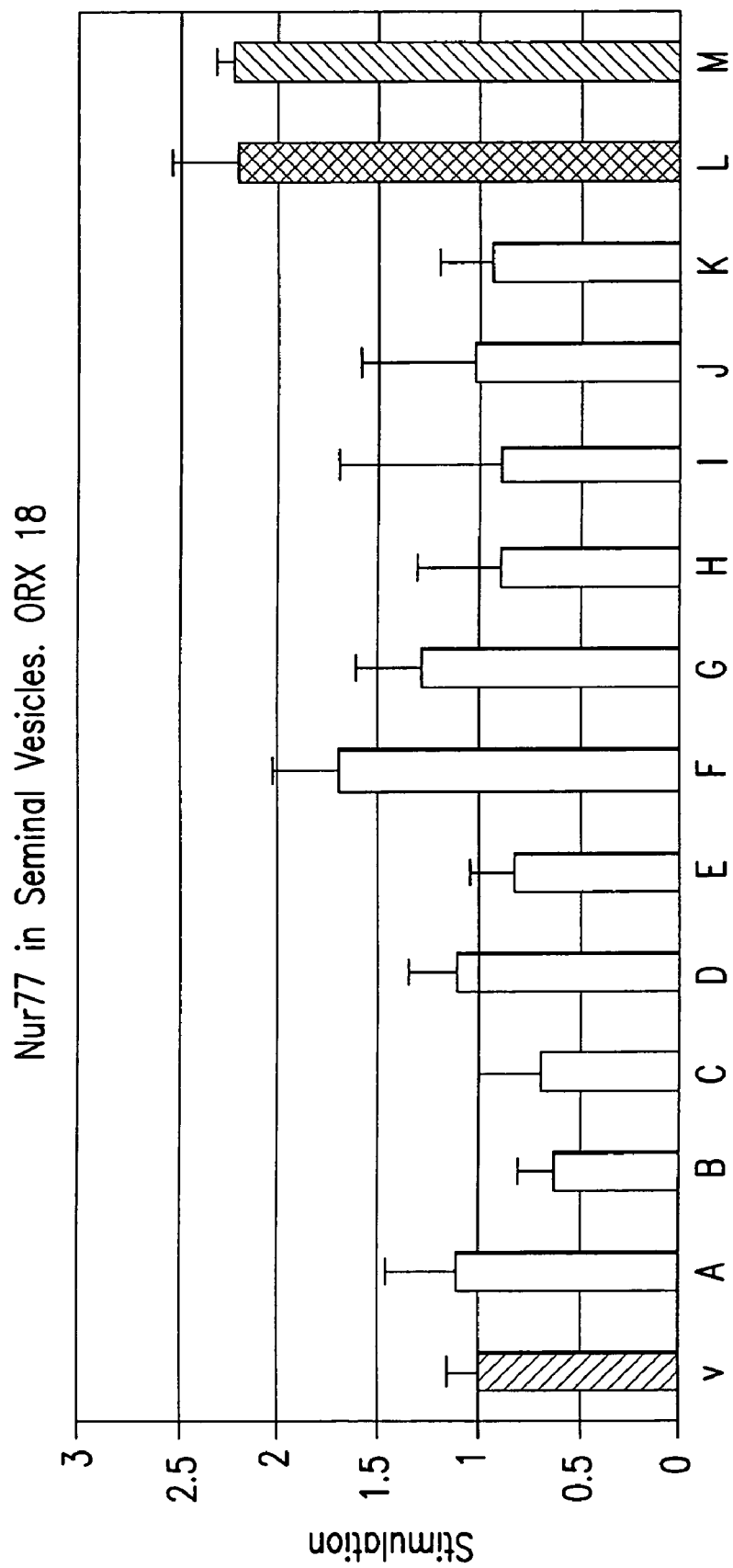
FIG. 6 shows that expression of Nur77 in orchiectomized (ORX) rats can be modulated by DITF and various other SARM's. Compounds A through L are SARM's. In particular, I is flutamide, and J is cyproterone acetate. M is dihydrotestosterone. V is vehicle.

Other researchers have shown that parathyroid hormone can regulate Nur77 expression in bone (Tetradis et al., in Biochem. Biophys. Res. Comm. 281: 913-916 (2001)) and LH can regulate Nur77 expression in testicular Leydig cells (Song et al., Endocrinol. 142: 5116-5123 (2001). Promyelocytic leukemia protein PML is a tumor and growth suppresser that inhibits Nur77-mediated transcription by interacting with the DNA-binding domain of Nur77, which prevents it from binding its target promoter (Wu et al., oncogene 21: 3925-3933 (2002). The role of Nur77 in signal transduction has been discussed by Winoto and Littman, Cell 109: S57-S66 (2002). The inventors show in FIG. 5 that the androgen, DHT, and several other selective androgen receptor modulators (SARM's) can control to various extents the expression of Nur77 in prostrate cancer cells and in FIG. 6 that DHT and various other SARM's can modulate to various extents Nur77 expression in the seminal vesicles of orchiectomized (ORX) rats.

In light of the above, analytes identified by the assays disclosed herein may be useful for treating a wide variety of diseases and disorders. Analytes that affect Nur77 expression or activity may be useful for treating or inhibiting inflammatory diseases, for example, osteoarthritis, and various bone, neurological, and prostrate disorders. Analytes that bind Nur77 may also be useful for treating cancer, for example, prostrate, lung, ovarian, gastric, and colon cancer. The nucleic acid encoding the rhNur77 is further useful for providing recombinant rhNur77 (full-length or fragments comprising domains thereof such as the LBD or the DBD) for crystallographic structural studies on rhNur77 or its domains and their interaction with various binding partners and analytes. The rhNur77 or fragments thereof may also be useful in treatments for particular cancers, for example, lung cancer, prostrate cancer, colon cancer, ovarian cancer, and gastric cancer. For example, recombinant rhNur77 in which the DBD is removed, modified so as not to be capable of binding DNA, or inactivated can be used to induce apoptosis in cancer cells.

Therefore, in a first aspect, the present invention provides nucleic acid molecules which encode the rhNur77. The isolated nucleic acid molecules include both deoxyribonucleic acid (DNA) and ribonucleic acid (RNA) molecules encoding the rhNur77. The isolated nucleic acid molecules further include genomic DNA and complementary DNA (cDNA) encoding the rhNur77, either of which can be single- or double-stranded, as well as synthetic DNA, such as a synthesized, single stranded polynucleotide. When single-stranded, the DNA molecule can comprise either the coding (sense) strand or the non-coding (antisense) strand. The nucleic acids encoding the rhNur77 have a nucleotide sequence substantially similar to the nucleotide sequence set forth in SEQ ID NO:1 (FIG. 1). For most cloning purposes, DNA is the preferred nucleic acid. In the case of nucleic acid molecules isolated from genomic DNA, the nucleic acid sequences encoding the rhNur77 comprising the amino acid sequence in SEQ ID NO:2 can be interrupted by one or more introns. Therefore, in a further aspect of the present invention, rhNur77 polypeptides are provided which have an amino acid sequence which is substantially similar to the amino acid sequence set forth SEQ ID NO:2 (FIG. 2) and nucleic acids which encode the rhNur77 polypeptides for use in the analyte screening assays disclosed herein.

As used herein, the term "substantially similar" with respect to SEQ ID NO:2 means that the rhNur77 contains mutations such as amino acid substitution or deletion mutations which do not abrogate the ability of the rhNur77 to bind at least one of its binding partners or activate transcription from a Nur77 responsive promoter. The mutations include naturally occurring allelic variants and variants produced by recombinant DNA methods. As used herein, the term "substantially similar" with respect to SEQ ID NO:1 means that the rhNur77 encoded by the nucleic acid contains mutations such as nucleotide substitution or deletion mutations which do not abrogate the ability of the rhNur77 to bind at least one of its binding partners or to activate transcription from a Nur77 responsive promoter. The mutations include naturally occurring allelic variants and variants produced by recombinant DNA methods. In general, any of the foregoing mutations which do not abrogate the ability of rhNur77 to bind at least one of its homologous or heterologous binding partners or activate transcription from a Nur77 responsive promoter are conservative mutations.

The present invention further includes a nucleic acid which encodes a biologically active fragment or mutant of the rhNur77. In general, the nucleic acid will encode either a polypeptide or polypeptide fragment, which at least substantially mimics the properties or activity of the rhNur77 or a particular domain of the rhNur77, for example, a nucleic acid encoding the ligand binding domain (LBD) from about nucleotide 997 to about nucleotide 1698, the DNA binding domain (DBD) from about nucleotide 800 to about nucleotide 996, the amino-terminal transactivation function 1 (AF1) from about nucleotide 1 to about nucleotide 799, and the carboxy-terminal activation domain 2 (AF2) from about nucleotide 1699 to about nucleotide 1797. The above nucleic acid can comprise one or more nucleotide substitutions, deletions, additions, amino-terminal truncations, and carboxy-terminal truncations which do not substantially abrogate the properties or activities of the rhNur77 or particular domain produced therefrom. Thus, the mutations of the present invention encode mRNA molecules that express an rhNur77 in a eukaryotic cell which has sufficient activity (ability to bind one or more of its binding partners or activate transcription from a Nur77 responsive promoter) to be useful in drug discovery.

The present invention further includes synthetic DNAs (sDNA) which encode the rhNur77 wherein the nucleotide sequence of the sDNA differs from the nucleotide sequence of SEQ ID NO:1 but still encodes the rhNur77 having the amino acid sequence as set forth in SEQ ID NO:2. For example, to express or enhance expression of the rhNur77 in a particular cell type, it may be necessary to change the sequence comprising one or more of the codons encoding the rhNur77 to a sequence which enables expression of the rhNur77 in the particular cell type. Such changes include modifications for codon usage peculiar to a particular host or removing cryptic cleavage or regulatory sites which would interfere with expression of the rhNur77 in a particular cell type. Therefore, the present invention discloses codon redundancies which may result in numerous DNA molecules expressing an identical protein. For purposes of this specification, a sequence bearing one or more replaced codons will be defined as a degenerate variation. Also included within the scope of this invention are mutations either in the DNA sequence or the translated protein that do not alter or do not substantially alter the ultimate physical or functional properties of the expressed protein (in general, these mutations are referred to as conservative mutations). For example, substitution of valine for leucine, arginine for lysine, or asparagine for glutamine may not cause a change in the functionality of the polypeptide.

It is known that DNA sequences encoding a peptide may be altered so as to code for a peptide that has properties that are different than those of the naturally occurring peptide. Methods for altering the DNA sequences include, but are not limited to, site-directed mutagenesis. Examples of altered properties include, but are not limited to, changes in the affinity of an enzyme for a substrate or a receptor for a ligand. In a particular embodiment, the present invention provides an isolated nucleic acid molecule comprising a sequence which encodes a mutated rhNur77 comprising the sequence set forth in SEQ ID NO:2 with about 1 to 10 amino acid additions, deletions, or substitutions, wherein the mutated rhNur77 binds at least a homologous or heterologous RXR, preferably a human RXR, or binds a nucleic acid comprising at least one NBRE binding site, or activates transcription from a natural or composite (synthetic) Nur77 responsive promoter.

Included in the present invention are nucleic acid sequences that hybridize to a nucleotide sequence in SEQ ID NO:1 under stringent conditions. By way of example, and not limitation, a procedure using conditions of high stringency is as follows. Prehybridization of filters containing nucleic acid molecules which might hybridize to a nucleotide sequence of SEQ ID NO:1 immobilized thereon is carried out for about two hours to overnight at about 65° C. in buffer composed of 6×SSC, 5× Denhardt's solution, and 100 µg/ml denatured salmon sperm DNA. Filters are hybridized for about 12 to 48 hrs at 65° C. in prehybridization mixture containing 100 µg/ml denatured salmon sperm DNA and 5-20×10$^6$ counts-per-minute of $^{32}$P-labeled nucleic acid probe comprising at least 10 contiguous nucleotides of the nucleotide sequence in SEQ ID NO:1. Washing of filters is done at 37° C. for about 1 hour in a solution containing 2×SSC, 0.1% SDS. This is followed by a wash in 0.1×SSC, 0.1% SDS at 50° C. for 45 minutes before detecting bound probe by autoradiography. Other procedures using conditions of high stringency would include either a hybridization step carried out in 5×SSC, 5× Denhardt's solution, 50% formamide at about 42° C. for about 12 to 48 hours or a washing step carried out in 0.2× SSPE, 0.2% SDS at about 65° C. for about 30 to 60 minutes. Reagents mentioned in the foregoing procedures for carrying out high stringency hybridization are well known in the art. Details of the composition of these reagents can be found in Sambrook et al., Molecular Cloning: A Laboratory Manual 2$^{nd}$ Edition; Cold Spring Harbor Laboratory Press, Cold Spring Harbor, N.Y., (1989) or Sambrook and Russell, Molecular Cloning: A Laboratory Manual, 3rd Edition. Cold Spring Harbor Laboratory Press, Plainview, N.Y. (2001). In addition to the foregoing, other conditions of high stringency which may be used are also well known in the art.

In an another aspect of the present invention, a substantially purified form of an rhNur77 which comprises a sequence of amino acids as disclosed in FIG. 2 (SEQ ID NO:2) is provided. Further provided are polypeptide fragments and/or mutants of the rhNur77, preferably bioactive polypeptide fragments, which comprise at least a portion of the amino acid sequence set forth in SEQ ID NO: 2. By way of example, a polypeptide fragment of rhNur77 can comprise the LBD from about amino acid 333 to about amino acid 566, DBD from about amino acid 267 to about amino acid 332, AF1 from about amino acid 1 to about amino acid 266, and AF2 from about amino acid 567 to about amino acid 598. These mutations or polypeptide fragments include, but are not limited to, amino acid substitutions, deletions, additions, amino terminal truncations, and carboxy-terminal truncations such that these mutations provide for proteins or protein fragments of diagnostic, therapeutic, or prophylactic use and are useful for screening assays for identifying analytes which interfere with the interaction of rhNur77 and one or more homologous or heterologous binding partners or its ability to activate transcription from a Nur77 responsive promoter, such analytes being useful for treatment of inflammatory diseases, for example, osteoarthritis and various bone, neurological, and prostrate disorders. Particular analytes may also be useful for treating cancers, for example, prostrate, lung, ovarian, gastric, and colon cancer. The above polypeptides and fragments are useful for X-ray crystallography studies on the structure of particular domains of the rhNur77 and their interactions with particular binding partners or analytes.

The rhNur77 polypeptides of the present invention can be the "mature" protein or a fragment or portion thereof, any of which can be a part of a larger protein such as to provide a fusion or chimeric protein. It is often advantageous to include covalently linked to the amino acid sequence of the rhNur77, an additional amino acid sequence which contains secretory or leader sequences, pro-sequences, sequences which aid in purification of the rhNur77 such as multiple histidine residues (polyHis) or antibody-binding epitopes, or one or more additional amino acid sequences which confer stability to the rhNur77 during recombinant production. Thus, rhNur77 fusion proteins are provided which comprise all or part of the rhNur77 linked at its amino or carboxyl terminus to proteins or polypeptides such as green fluorescent protein (GFP), c-myc epitope, alkaline phosphatase, protein A or G, glutathione S-transferase (GST), polyHis, peptide cleavage site, or antibody Fc region. In particular aspects of the fusion protein, the fusion protein can comprise the rhNur77 LBD fused to the DBD of another protein, for example, the Nur77 LBD, AF1, AF2, or combinations thereof is fused to the DBD of the glucocorticoid receptor (GR) or the DBD of the yeast GAL4 protein. Any of the foregoing fusion constructs can be expressed in a cell line of interest and used to screen for modulators of the rhNur77 disclosed herein. The present invention further provides an isolated nucleic acid molecule comprising a sequence which encodes a fusion rhNur77 comprising all or a part of the sequence set forth in SEQ ID NO:2 or a mutated variant thereof in which the mutation comprises about 1-10 amino acid additions, deletions, or substitutions, operably linked to a nucleic acid encoding a second protein or fragment thereof including mutants thereof.

The present invention further provides vectors which comprise at least one of the nucleic acid molecules disclosed throughout this specification, preferably wherein the nucleic acid molecule is operably linked to a heterologous promoter. These vectors can comprise DNA or RNA. For most cloning purposes, DNA plasmid or viral expression vectors are preferred. Typical expression vectors include plasmids, modified viruses, bacteriophage, cosmids, yeast artificial chromosomes, and other forms of episomal or integrated DNA, any of which expresses the rhNur77, polypeptide fragment thereof, or fusion protein comprising all or part of the rhNur77 encoded therein. It is well within the purview of the skilled artisan to determine an appropriate vector for a particular gene transfer or other use. As used herein, the term "recombinant rhNur77" is intended to include any variation of rhNur77 disclosed herein which is expressed from a vector transfected into a eukaryote cell or transformed into a prokaryote cell. Transfected eukaryote cells and transformed prokaryote cells are referred to as recombinant host cells.

An expression vector containing DNA encoding a rhNur77 or any one of the aforementioned variations thereof wherein the DNA is preferably operably linked to a heterologous promoter can be used for expression of the recombinant rhNur77 in a recombinant host cell. Such recombinant host cells can be cultured under suitable conditions to produce recombinant rhNur77 or a biologically equivalent form. Expression vectors include, but are not limited to, cloning vectors, modified cloning vectors, specifically designed plasmids, or specifically designed viruses. As used herein, the term "variants" includes both mutants and fragments of the rhNur77.

Commercially available mammalian expression vectors which are suitable for recombinant rhNur77 expression include, but are not limited to, pcDNA3.neo (Invitrogen, Carlsbad, Calif.), pcDNA3.1 (Invitrogen), pcDNA3.1/Myc-His (Invitrogen), pCI-neo (Promega, Madison, Wis.), pLITMUS28, pLITMUS29, pLITMUS38 and pLITMUS39 (New England Bioloabs, Beverly, Mass.), pcDNAI, pcDNAIamp (Invitrogen), pcDNA3 (Invitrogen), pMCI-neo (Stratagene, La Jolla, Calif.), pXT1 (Stratagene), pSG5 (Stratagene), EBO-pSV2-neo (ATCC 37593) pBPV-1(8-2) (ATCC 37110), pdBPV-MMTneo (342-12) (ATCC 37224), pRS-Vgpt (ATCC 37199), pRSVneo (ATCC 37198), pSV2-dhfr (ATCC 37146), pUCTag (ATCC 37460), and 1ZD35 (ATCC 37565).

Also, a variety of bacterial expression vectors can be used to express recombinant rhNur77 in bacterial cells. Commercially available bacterial expression vectors, which may be suitable for recombinant rhNur77 expression include, but are not limited to, pCR2.1 (Invitrogen), pET 11 a (Novagen, Madison, Wis.), lambda gt11 (Invitrogen), pCR4Blunt-TOPO (Invitrogen), and pKK223-3 (Pharmacia).

In addition, a variety of fungal cell expression vectors may be used to express recombinant rhNur77 in fungal cells. Commercially available fungal cell expression vectors which are suitable for recombinant rhNur77 expression include, but are not limited to, pYES2 (Invitrogen) and *Pichia* expression vector (Invitrogen).

Also, a variety of insect cell expression vectors can be used to express recombinant rhNur77 in insect cells. Commercially available insect cell expression vectors which can be suitable for recombinant expression of rhNur77 include, but are not limited to, pBlueBacIII and pBlueBacHis2 (Invitrogen), and pAcG2T (Pharmingen).

Viral vectors which can be used for expression of recombinant rhNur77 include, but are not limited to, adenovirus vectors, adeno-associated virus vectors, herpesvirus vectors, Sindbis virus vectors, Simliki forest virus vectors, pox virus vectors (such as vaccinia virus, fowl pox, canary pox, and the like), retrovirus vectors, and baculovirus vectors. Many of viral vectors are commercially available.

The present invention further provides recombinant host cells transformed or transfected with a vector comprising any one of the aforementioned nucleic acid molecules, particularly host cells transformed or transfected with a vector comprising any one of the aforementioned nucleic acid molecules wherein the nucleic acid molecule is operably linked to a promoter. Recombinant host cells include bacteria such as *E. coli*, fungal cells such as yeast, plant cells, mammalian cells including, but not limited to, cells of bovine, porcine, monkey, human, or rodent origin; and insect cells including, but not limited to, *Drosophila* and silkworm-derived cell lines. For instance, one insect expression system utilizes *Spodoptera frugiperda* (Sf21) insect cells (Invitrogen) in tandem with a baculovirus expression vector (pAcG2T, Pharmingen, San Diego, Calif.). Mammalian cells include primary cultures of chondrocytes, osteoblasts, synovial cells, and the like. Also, mammalian cell lines, which may be suitable, include but are not limited to, 22Rv1 cells (ATCC CRL-2505), LnCap cells (ATCC CRL-1740), hFOB 1.19 cells (ATCC CRL 11372), 7F2 cells (ATCC CRL 12557), SaOs-2 cells (ATCC HTB-85, MC3T3T3 cells (ATCC CRL-2593), HIG82 cells (ATCC CRL-1832), C-28/12 cells, T/C-28a2 cells, T/C-28a4, JEG3 cells, L cells L-M(TK−) (ATCC CCL-1.3), L cells L-M (ATCC CCL-1.2), 293 cells (ATCC CRL-1573), Raji cells (ATCC CCL-86), CV-1 cells (ATCC CCL-70), COS-1 cells (ATCC CRL-1650), COS-7 cells (ATCC CRL-1651), CHO-K1 cells (ATCC CCL-61), 3T3 cells (ATCC CCL-92), NIH/3T3 cells (ATCC CRL-1658), HeLa cells (ATCC CCL-2), C127I cells (ATCC CRL-1616), BS-C-1 cells (ATCC CCL-26), MRC-5 cells (ATCC CCL-171), HEK293T cells (ATCC CRL-1573), ST2 cells (Riken Cell bank, Tokyo, Japan RCB0224), C3H10T1/2 cells (JCRB0602, JCRB9080, JCRB0003, or IF050415), and CPAE cells (ATCC CCL-209). Such recombinant host cells can be cultured under suitable conditions to produce rhNur77 or a biologically equivalent form.

As noted above, an expression vector containing DNA encoding rhNur77 or any one of the aforementioned variations thereof can be used to express the rhNur77 encoded therein in a recombinant host cell. Therefore, the present invention provides a process for expressing a rhNur77 or any one of the aforementioned variations thereof in a recombinant host cell comprising introducing the vector comprising a nucleic acid which encodes the rhNur77 into a suitable host cell and culturing the host cell under conditions which allow expression of the rhNur77. In a further aspect, the rhNur77 has an amino acid sequence substantially as set forth in SEQ ID NO:2 and binds at least one homologous or heterologous rhNur77 binding partner such as RXR or nucleic acid comprising at least one Nur77 binding site, or activates transcription from a Nur77 responsive promoter and the nucleic acid encoding the rhNur77 or variation thereof is operably linked to a heterologous promoter which can be constitutive or inducible. Examples of Nur77 responsive promoters include promoters such as the promoter for the gene encoding NGFI-B protein, pro-opiomelanocortin (POMC), or retinoid acid receptor (RAR), or composite promoters comprising one or more copies of a Nur77 responsive sequence, for example, a composite promoter comprising an NGFI-B (Nur77)-responsive element (NBRE), a Nur77 response element (NurRE) or an RA response element (βRARE) in the RARβ promoter operably linked to a heterologous promoter such as the CMVie or HSV thymidine kinase (TK) promoter. Thus, the present invention further provides a cell comprising a nucleic acid encoding the rhNur77 or variation thereof which has an amino acid sequence substantially as set forth in SEQ ID NO:2, which preferably binds at least one homologous or heterologous binding partner such as RXR or nucleic acid comprising at least one Nur77 binding site, or activates a Nur77 responsive promoter, and wherein the nucleic acid encoding the rhNur77 is operably linked to a heterologous promoter.

The nucleic acids of the present invention are preferably assembled into an expression cassette that comprises sequences which provide for efficient expression of the rhNur77 or variant thereof as described previously encoded thereon in a mammalian cells such as a human cell. The cassette preferably contains the full-length cDNA encoding the rhNur77 or a DNA encoding a fragment of the rhNur77 with homologous or heterologous transcriptional and translational control sequences operably linked to the DNA. Such control sequences include at least a transcription promoter (constitutive or inducible) and transcription termination sequences and can further include other regulatory elements such as transcription enhancers, ribosome binding sequences, splice junction sequences, and the like. In most aspects, the promoter is a heterologous promoter; however, in particular aspects, the promoter can the natural rhNur77 promoter for ectopic expression of the rhNur77 in various host cells of non-rhesus monkey origin. In a particularly useful aspect, the promoter is the constitutive cytomegalovirus immediate early promoter with or without the intron A sequence (CMV) although those skilled in the art will recognize that any of a number of other known promoters such as the strong immunoglobulin promoter, Rous sarcoma virus long terminal repeat promoter, SV40 small or large T antigen promoter, or the like. A preferred transcriptional terminator is the bovine growth hormone terminator although other known transcriptional terminators such as SV40 termination sequences can also be used. The combination of an expression cassette comprising the rhNur77 operably linked to the CMV promoter and the BGH terminator can provide suitable expression of cDNA encoding the rhNur77 in eukaryote cells.

Following expression of rhNur77 or any one of the aforementioned variations of the rhNur77 in a host cell, rhNur77 or variant thereof can be recovered to provide rhNur77 in a form capable of binding one or more homologous or heterologous Nur77 binding partners or activate transcription from a Nur77 responsive promoter. Several rhNur77 purification procedures are available and suitable for use. The rhNur77 can be purified from cell lysates and extracts by various combinations of, or individual application of salt fractionation, ion exchange chromatography, size exclusion chromatography, hydroxylapatite adsorption chromatography, or hydrophobic interaction chromatography. In addition, rhNur77 can be separated from other cellular polypeptides by use of an immunoaffinity column made with monoclonal or polyclonal antibodies specific for rhNur77 or a particular epitope thereof. Alternatively, in the case of fusion polypeptides comprising all or a portion of the rhNur77 fused to a second polypeptide, purification can be achieved by affinity chromatography comprising a reagent specific for the second polypeptide such as an antibody or metal.

Methods for cloning, constructing expression vectors, producing recombinant host cells, including transiently or stably transfected eukaryote cells, protein isolation, and the like are well known in the art and can be found for example in Sambrook et al., Molecular Cloning: A Laboratory Manual 2nd Edition; Cold Spring Harbor Laboratory Press, Cold Spring Harbor, N.Y., (1989) or Sambrook and Russell, Molecular Cloning: A Laboratory Manual, 3rd Edition. Cold Spring Harbor Laboratory Press, Plainview, N.Y. (2001)).

In accordance with yet another embodiment of the present invention, there are provided antibodies having specific affinity for the rhNur77 or fragment or epitope thereof. The term "antibodies" is intended to be a generic term which includes polyclonal antibodies, monoclonal antibodies, Fab fragments, single $V_H$ chain antibodies such as those derived from a library of camel or llama antibodies or camelized antibodies (Nuttall et al., Curr. Pharm. Biotechnol. 1: 253-263 (2000); Muyldermans, J. Biotechnol. 74: 277-302 (2001)), and recombinant antibodies. The term "recombinant antibodies" is intended to be a generic term which includes single polypeptide chains comprising the polypeptide sequence of a whole heavy chain antibody or only the amino terminal variable domain of the single heavy chain antibody ($V_H$ chain polypeptides) and single polypeptide chains comprising the variable light chain domain ($V_L$) linked to the variable heavy chain domain ($V_H$) to provide a single recombinant polypeptide comprising the Fv region of the antibody molecule (scFv polypeptides)(See, Schmiedl et al., J. Immunol. Meth. 242: 101-114 (2000); Schultz et al., Cancer Res. 60: 6663-6669 (2000); Dübel et al., J. Immunol. Meth. 178: 201-209 (1995); and in U.S. Pat. No. 6,207,804 B1 to Huston et al.).

Construction of recombinant single $V_H$ chain or scFv polypeptides which are specific against an analyte can be obtained using currently available molecular techniques such as phage display (de Haard et al., J. Biol. Chem. 274: 18218-18230 (1999); Saviranta et al., Bioconjugate 9: 725-735 (1999); de Greeff et al., Infect. Immun. 68: 3949-3955 (2000)) or polypeptide synthesis. In further aspects, the recombinant antibodies include modifications such as polypeptides having particular amino acid residues or ligands or labels such as horseradish peroxidase, alkaline phosphatase, fluors, and the like. Further still aspects include fusion polypeptides which comprise the above polypeptides fused to a second polypeptide such as a polypeptide comprising protein A or G.

The antibodies specific for rhNur77 can be produced by methods known in the art. For example, polyclonal and monoclonal antibodies can be produced by methods well known in the art, as described, for example, in Harlow and Lane, Antibodies: A Laboratory Manual. Cold Spring Harbor Laboratory Press: Cold Spring Harbor, N.Y. (1988). RhNur77 or fragments or epitopes thereof can be used as immunogens for generating such antibodies. Alternatively, synthetic peptides of particular regions of the rhNur77 can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, camelized, CDR-grafted, or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (See, for example, Bahouth et al., Trends Pharmacol. Sci. 12: 338 (1991); Ausubel et al., Current Protocols in Molecular Biology (John Wiley and Sons, N.Y. (1989)).

Antibodies so produced can be used for the immunoaffinity or affinity chromatography purification of the rhNur77 or rhNur77/binding partner complexes. The above referenced anti-rhNur77 antibodies can also be used to modulate the activity of the rhNur77 in living animals, in humans, or in biological tissues isolated therefrom. Accordingly, contemplated herein are compositions comprising a carrier and an amount of an antibody having specificity for rhNur77 effective to block naturally occurring rhNur77 from binding to a Nur77 binding partner or activate transcription from a Nur77 responsive promoter.

Therefore, the nucleic acids encoding rhNur77 or variants thereof, vectors containing same, host cells transformed with the nucleic acids or vectors which express the rhNur77 or variants thereof, the expressed rhNur77 or variants thereof, as well as antibodies specific for rhNur77, can be used in in vivo or in vitro methods for screening a plurality of analytes to identify analytes which are modulators of the rhNur77/binding partner interaction or transcription activation. These methods provide information regarding the function and activity of the rhNur77 or variants thereof which can lead to the identification and design of molecule, compounds, or compositions capable of specific interactions with Nur77.

Therefore, the nucleic acids encoding rhNur77 or variant thereof, vectors containing same, host cells transformed with the nucleic acids or vectors which express the rhNur77 or variants thereof, the rhNur77 and variants thereof, as well as antibodies specific for the rhNur77, can be used in in vivo or in vitro methods for screening a plurality of analytes to identify analytes which are modulators of the rhNur77/Nur77 binding partner (RXR, co-activator, other ligand, or nucleic acid comprising at least one Nur77 binding site) interaction. These methods provide information regarding the function and activity of the rhNur77 and variants thereof which can lead to the identification and design of molecule, compounds, or compositions capable of specific interactions with human rhNur77. In preferred aspects, the methods identify analytes that interfere with the binding of the rhNur77 to a homologous or heterologous Nur77 binding partner involved in the various cellular signaling pathways. Such analytes may be useful either alone or in combination with other compounds for treating or inhibiting inflammatory diseases such as osteoarthritis and various bone, neurological, and prostrate disorders, and for treating cancers, for example, prostrate, colon, ovarian, lung, and gastric cancers.

Accordingly, in a further aspect, the present invention provides methods (screening assays) for identifying analytes that modulate the activity of rhNur77, the binding of rhNur77 to one or more homologous or heterologous binding partners, or expression of Nur77. That is, screening methods for identifying candidates or test compounds or agents, for example, peptides, peptidomimetics, small molecules, or other drugs. Modulators can include, for example, full or partial agonists or antagonists or analytes that selectively modulate rhNur77 activity in a promoter and cell context-dependent manner. Modulation of Nur77 activity or binding to an rhNur77 binding partner includes, for example, analytes that modulate rhNur77 activity by binding to the LBD of the rhNur77, analytes that modulate phosphorylation of the rhNur77, analytes that modulate the half-life of the rhNur77, and analytes that modulate expression of the rhNur77. Modulators of rhNur77 can be full or partial agonists or antagonists. Modulators further include analytes that exert their effect in a tissue specific manner. That is the analyte selectively modulates rhNur77 activity in a promoter and cell-context dependent manner, e.g., the analyte either partially or fully activates or represses expression of one gene or gene product while stimulating or repressing the expression of a second gene or gene product. In a preferred aspect, the present invention provides methods for identifying analytes which modulate binding of rhNur77 to its protein or nucleic acid binding partner. In general, analytes which modulate binding of rhNur77 to its binding partner either bind the rhNur77 or the binding partner and the binding modulates the binding of the Nur77 to its binding partner.

In preferred aspects, the screening methods disclosed herein are useful for identifying analytes which bind to the site or domain of rhNur77 that is involved in binding to a particular Nur77 binding partner or to a site or domain on the Nur77 binding partner which is involved in binding to the rhNur77. In either case, the screening methods identify analytes which interfere with the binding of rhNur77 to a Nur77 binding partner. The interference in binding can be measured directly by identifying the rhNur77/Nur77 binding partner complex or indirectly by monitoring a downstream cellular response to the interference in binding such as activation of a reporter gene responsive to the interference in binding.

Methods for identifying analytes which modulate (interfere with, inhibit, suppress, or stimulate) binding of rhNur77 to one or more homologous or heterologous Nur77 binding partners (preferably, a heterologous Nur77 binding partner, most preferably a heterologous Nur77 binding partner of human origin) include (i) cell-based binding methods for identifying analytes which modulate rhNur77 activity or inhibit or stimulate binding between rhNur77 and at least one homologous or heterologous Nur77 binding partner; and (ii) cell-free binding methods for identifying analytes which inhibit binding between rhNur77 protein and at least one homologous or heterologous Nur77 binding partner or nucleic acid comprising one or more Nur77 binding sites. Therefore, while the methods disclosed herein use the rhNur77 and nucleic acids encoding the same, the Nur77 binding partner and nucleic acids encoding the same (where appropriate) are not limited to those obtained from the rhesus monkey but can include those polypeptides and nucleic acids encoding the same from other mammals such as humans.

In one aspect, the invention provides methods for screening a plurality of analytes for analytes which bind to or modulate the activity of rhNur77 or polypeptide or biologically active portion thereof. In another aspect, the invention provides methods for screening a plurality of analytes for analytes which bind to or modulate the activity of Nur77 binding partner. The plurality of analytes can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer, or small molecule libraries of compounds (Lam, Anticancer Drug Des. 12: 145 (1997)).

Examples of methods for synthesizing molecular libraries can be found in the art, for example, DeWitt et al., Proc. Natl. Acad. Sci. USA 90: 6909 (1993); Erb et al., Proc. Natl. Acad. Sci. USA 91: 11422 (1994); Zuckermann et al., J. Med. Chem. 37: 2678 (1994); Cho et al., Science 261: 1303 (1993); Carrell et al., Angew. Chem. Int. Ed. Engl. 33: 2059 (1994); Carell et al., Angew. Chem. Int. Ed. Engl. 33: 2061 (1994); and in Gallop et al., J. Med. Chem. 37: 1233 (1994).

Libraries of analytes can be presented in solution (for example, Houghten, Biotech. 13: 412421 (1992)), or on beads (Lam, Nature 354: 82-84 (1991)), chips (Fodor Nature, 364: 555-556 (1993)), bacteria or spore (U.S. Pat. No. 5,223,409 to Ladner), plasmids (Cull et al., Proc Natl. Acad. Sci. USA 89: 1865-1869 (1992)) or on phage (Scott and Smith, Science 249: 386-390 (1990); Devlin, Science 249: 404406 (1990); Cwirla et al., Proc. Natl. Acad. Sci. USA 87: 6378-6382 (1990); Felici J. Mol. Biol. 222:301-310(1991); and, U.S. Pat. No. 5,223,409 to Ladner).

In the various embodiments of the cell-based and cell-free methods disclosed herein, the Nur77 binding partner is preferably obtained from an organism selected from the group consisting of mouse, rat, dog, and human. More preferably, the Nur77 binding partner is of human origin. The Nur77 binding partner is preferably selected from the group consisting of RXR and nucleic acid comprising at least one Nur77 binding site.

The present invention provides a cell-based screening method for identifying analytes which modulate the rhNur77's ability to stimulate transcription of a reporter gene operably linked to a promoter comprising an Nur77 binding site. The method entails co-transfecting into a mammalian cell a first vector which comprises a gene expression cassette comprising a nucleic acid encoding the rhNur77 operably linked to a promoter and a second vector which comprises a gene expression cassette comprising a reporter gene encoding a detectable product operably linked to a promoter containing at least one Nur77 binding site. The promoter regulating expression of the rhNur77 can be a heterologous promoter which is either inducible or a constitutive. The promoter regulating expression of the reporter gene includes promoters such as the promoter for the gene encoding NGFI-B protein, the pro-opiomelanocortin (POMC), or the retinoid acid receptor (RAR), including composite promoters comprising one or more copies of a Nur77 responsive sequence, for example, an NGFI-B (Nur77)-responsive element (NBRE), a Nur77 response element (NurRE) or an RA response element (βRARE) in the RARβ promoter operably linked to a heterologous promoter such as the CMVie or HSV thymidine kinase (TK) promoter. Reporter genes which are useful in the cell-based assays of the present invention include, but are not limited to, the luciferase gene, green fluorescent protein, secreted alkaline phosphatase (SEAP), placental alkaline phosphatase (PLAP), β-galactosidase gene, β-lactamase gene, and β-glucoronidase gene.

In a further aspect of the above cell-based method, the first gene expression cassette comprises a nucleic acid encoding a fusion protein comprising the LBD of the rhNur77 fused to the yeast GAL4 DBD and the second expression cassette comprises a nucleic acid encoding a reporter gene operably linked to a promoter comprising at least one copy of recognition site for the GAL4 DBD. The rhNur77 LBD encoded by the nucleic acid comprises the amino acids from about position 333 to about position 566 and the GAL4 DBD comprises the amino acids from about position 1 to about position 147.

In a further still aspect of the above cell-based method, the first gene expression cassette comprises a nucleic acid encoding a fusion or chimeric protein comprising the LBD of the rhNur77 fused to the glucocorticoid receptor (GR) DBD and the second expression cassette comprises a nucleic acid encoding a reporter gene operably linked to a promoter comprising at least one copy of a recognition site for the GR DBD. The rhNur77 LBD encoded by the nucleic acid comprises the amino acids from about position 333 to about position 566 and the GR DBD comprises the amino acids from about position 1 to about position 505.

In a typical assay for antagonists or agonists, the cells transfected with the above vectors comprising any one of the above embodiments are incubated in a medium containing the analyte to be tested for antagonist or agonist activity. During the incubation period or a suitable period of time after commencing the incubation period, expression of the reporter gene is measured. In general, a positive control is also provided in which the transfected cells are incubated in a medium without the analyte and a negative control is provided in which the transfected cells are incubated in a medium containing a known antagonist. A decrease in expression of the reporter gene relative to the positive control indicates that the analyte is an antagonist of Nur77 activity whereas an increase or enhancement in expression of the reporter gene relative to the positive control indicates that the analyte is an agonist of Nur77 activity.

The present invention further provides a cell-based method for identifying analytes which are agonists or antagonists of the interaction between RXR and the rhNur77. The method entails co-transfecting into a mammalian cell a first vector which comprises a gene expression cassette comprising a nucleic acid encoding the rhNur77 operably linked to a promoter, a second vector which comprises a gene expression cassette comprising a reporter gene encoding a detectable product operably linked to a promoter containing at least one Nur77 binding site, and a third vector which comprises a gene expression cassette comprising a nucleic acid encoding the RXR operably linked to a heterologous promoter. The expression cassettes are transfected into a cell and the cell incubated in a medium comprising an analyte to be tested for agonist or antagonist activity. An analyte which is an agonist causes an increase in reporter gene expression whereas an analyte which is an antagonist causes a decrease in reporter gene expression. The promoters regulating expression of the rhNur77 and the RXR can be heterologous promoters which are either inducible or a constitutive. The promoter regulating expression of the reporter gene is a promoter comprising one or more retinoid acid response elements, for example, promoter can be a composite promoter comprising the human retinoid acid receptor $^\beta 2$ (hRAR$^\beta 2$) gene promoter ($^\beta$RE) upstream of a thymidine kinase promoter. Reporter genes which are useful in the cell-based assays of the present invention include, but are not limited to, the luciferase gene, green fluorescent protein, secreted alkaline phosphatase (SEAP), placental alkaline phosphatase (PLAP), β-galactosidase gene, β-lactamase gene, and β-glucoronidase gene. In particular embodiments, the RXR is provided by co-transfecting the first and second vectors into a cell which expresses high levels of endogenous RXR, for example, human Hep2 cells express high levels of endogenous RXR.

In a further aspect for identifying agonists and antagonists of the rhNur77/RXR interaction, a two-hybrid assay is provided wherein the first gene expression cassette comprises a nucleic acid encoding a fusion protein comprising the LBD of the rhNur77 fused to the GAL4 DBD operably linked to a promoter, the second expression cassette comprises a nucleic acid encoding a reporter gene operably linked to a promoter comprising at least one copy of a recognition site for the GAL4 DBD, and the third expression cassette comprises a nucleic acid encoding a fusion protein comprising the LBD of RXR fused to the VP16 activation domain of herpes simplex virus (HSV) operably linked to a promoter. Preferably, the RXR LBD comprises the human RXRx from about amino acid 198 to about amino acid 462. The expression cassettes are transfected into a cell and the cell incubated in a medium comprising an analyte to be tested for inhibiting heterodimerization between the rhNur77 LBD and the RXR LBD.

A two-hybrid assay using a fusion protein consisting of a Nur77 LBD fused to the GAL4 DBD and the RXR LBD fused to the VP16 activation domain for defining the requirements for heterodimerization between related nuclear receptor Nurr1 and RXR was described in Aarnisalo et al., J. Biol. Chem. 277: 35118-35123 (2002).

In a further still aspect of the two-hybrid assay, the first gene expression cassette comprises a nucleic acid encoding a fusion protein comprising the LBD of the rhNur77 fused to the GR DBD operably linked to a promoter, the second expression cassette comprises a nucleic acid encoding a reporter gene operably linked to a promoter comprising at least one copy of a recognition site for the GR DBD, and the third expression cassette comprises a nucleic acid encoding a fusion protein comprising the LBD of RXR fused to the VP16 activation domain of herpes simplex virus (HSV) operably linked to a promoter. Preferably, the RXR LBD comprises the human RXRα from about amino acid 198 to about amino acid 462.

In a typical assay for agonists or antagonists, the cells transfected with the above vectors comprising any one of the above embodiments are incubated in a medium containing the analyte to be tested for antagonist or agonist activity. During the incubation period or a suitable period of time after commencing the incubation period, expression of the reporter gene is measured. In general, a control is also provided in which the transfected cells are incubated in a medium without the analyte and a negative control is provided in which the transfected cells are incubated in a medium containing a known antagonist. A decrease in expression of the reporter gene relative to the positive control indicates that the analyte is an antagonist of the Nur77-RXR interaction whereas an increase in expression of the reporter gene relative to the control indicates that the analyte is an agonist of the Nur77-RXR interaction.

In a further aspect of the above methods, the expression of the Nur77 is determined by measuring the amount of RNA encoding the Nur77 in the cell. In a further still aspect, the amount of RNA is measured by reverse-transcription polymerase chain reaction, preferably, the amount of RNA is measured by TAQMAN (Perkin Elmer) real-time quantitative polymerase chain reaction (PCR). In a further still aspect, the expression of the Nur77 is determined by measuring the amount of Nur77 polypeptide in the cell. In a further still aspect, the amount of Nur77 polypeptide is determined by using an antibody specific for the Nur77.

Cell-free screening assays are provided for identifying analytes which are agonists or antagonists of rhNur77 binding to a Nur77 binding partner. In one embodiment of a cell-free screening method, the method is a competition assay in which the ability of an analyte to effectively compete with the rhNur77 for binding to a homologous or heterologous Nur77 binding partner such as RXR, a co-activator, ligand, or nucleic acid comprising at least one Nur77 binding site is determined. Binding of the analyte can be determined either directly or indirectly. Binding can be determined using labeled or unlabeled antibodies against rhNur77, analyte, or Nur77 binding partner, the rhNur77/Nur77 binding partner complex, labeled rhNur77, and combinations thereof. Labels include, but are not limited to, radioactive isotopes, fluorescent dyes, enzymatic reporters such as alkaline phosphatase or horseradish peroxidase, donor-quencher fluorescent dyes, antibody recognition sites such as those provided by fusion polypeptides (for example, rhNur77 fused to alkaline phosphatase or a myc antibody recognition sequence).

In a further aspect, the method includes contacting the rhNur77 with the Nur77 binding partner to form a mixture, adding an analyte to the mixture, and determining the ability of the analyte to interfere with the binding of the rhNur77 to a Nur77 binding partner, e.g., RXR or a nucleic acid comprising one or more NBRE binding sites. Immunoprecipitation is a particular type of cell-free method which is useful for identifying analytes which inhibit binding of rhNur77 to a Nur77 binding partner.

In another aspect of a cell-free method, the rhNur77 is contacted with an analyte and the ability of the analyte to inhibit or suppress subsequent binding of the rhNur77 to a homologous or heterologous Nur77 binding partner is determined. Determining the ability of the analyte to inhibit or suppress binding of the rhNur77 can be detected as discussed above for cell-based methods. Determining the ability of the rhNur77 to bind to a Nur77 binding partner can also be accomplished using a technology such as real-time Biomolecular Interaction Analysis (BIA) (Sjolander and Urbaniczky, Anal. Chem. 63: 2338-2345 (1991) and Szabo et al., Curr. Opin. Struct. Biol. 5: 699-705 (1995)). As used herein, "BIA" is a technology for studying biospecific interactions in real time, without labeling any of the interactants (for example, BIACORE). Changes in the optical phenomenon surface plasmon resonance (SPR) can be used as an indication of real-time reactions between biological molecules.

In particular aspects of the above cell-free methods, it can be desirable to immobilize either rhNur77 or Nur77 binding partner to facilitate separation of rhNur77/Nur77 binding partner complexes from free rhNur77 and Nur77 binding partner, as well as to accommodate automation of the method. Binding of analyte to rhNur77, or interaction of a rhNur77 with a homologous or heterologous Nur77 binding partner in the presence and absence of an analyte, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/rhNur77 fusion proteins or glutathione-S-transferase/Nur77 binding partner can be adsorbed onto glutathione SEPHAROSE beads (Sigma Chemical, St. Louis, Mo.) or glutathione-derivatized microtitre plates, which are then combined with the analyte or the analyte and either the non-adsorbed Nur77 binding partner or rhNur77, and the mixture incubated under conditions conducive to complex formation (for example, at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix and the level of rhNur77 binding or activity determined using standard techniques.

Other methods for immobilizing proteins on matrices can also be used in the cell-free screening methods. For example, either rhNur77 or a Nur77 binding partner can be immobilized using a conjugation of biotin and streptavidin. Biotinylated protein or target molecules can be prepared from biotin-NHS(N-hydroxy-succinimide) using techniques well known in the art (for example, the biotinylation kit available from Pierce Biotechnology, Rockford, Ill.), and immobilized in the wells of streptavidin-coated 96 well plates (Pierce Biotechnology). Alternatively, antibodies reactive with rhNur77 or Nur77 binding partner but which do not interfere with binding of the rhNur77 to RXR can be derivatized to the wells of the plate, and unbound Nur77 binding partner or rhNur77 trapped in the wells by antibody conjugation. Methods for detecting such complexes, in addition to those described above for the GST-immobilized complexes, include immunodetection of complexes using antibodies reactive with the rhNur77 or Nur77 binding partner, as well as enzyme-linked assays which rely on detecting an enzymatic activity associated with the rhNur77 or Nur77 binding partner.

A further aspect of a cell-free binding method for identifying analytes which inhibit binding of rhNur77 to Nur77 binding partner is a modification of the GST fusion pull-down assay. The GST fusion pull-down assay has been described in Sambrook and Russell, Molecular Cloning: A Laboratory Manual 3rd Edition. Cold Spring Harbor Laboratory Press: Plainview, N.Y. (2001). A GST pull-down kit is available from Pierce Biotechnology. In the modified GST fusion pull-down assay used herein, either the DNA encoding rhNur77 or Nur77 binding partner is cloned in-frame with the GST of a pGEX vector (Amersham Pharmacia Bioscience, Piscataway, N.J.) and expressed as a GST fusion protein in the BL21 E. coli. The expressed GST fusion protein is bound to an immobilized reduced glutathione support. Preferably, the immobilized glutathione support is provided as a column. Labeled Nur77 binding partner or rhNur77 (labeled protein), respectively, is incubated with the bound GST fusion protein in the presence of an analyte. Afterwards, unbound labeled protein is removed and the GST fusion protein (bound or unbound to the labeled protein) is eluted from the support with imidazole. The amount of labeled protein bound to the eluted GST fusion protein is determined by detecting the label. If the analyte interferes with rhNur77 binding to the Nur77 binding partner, there will be little or no detectable labeled protein eluted with the GST fusion protein compared to controls without the analyte. Conversely, if the analyte does not interfere with rhNur77 binding to the Nur77 binding partner, the amount of labeled protein eluted with the GST fusion protein will be similar to the amount eluted in controls without the analyte.

It would be readily apparent to one of ordinary skill in the art that other cell-based or cell-free methods not disclosed herein can be adapted to use rhNur77 to identify analytes which inhibit or suppress binding of rhNur77 to a homologous or heterologous Nur77 binding partner. Therefore, the present invention is not limited to the methods disclosed herein but can include other assays provided the assay is adapted to use the rhNur77 or nucleic acids disclosed herein.

In many drug screening programs which screen libraries of analytes (drug, compounds, natural extracts, compositions, and the like), high throughput assays are desirable because they maximize the number of analytes that can be surveyed in a given period of time. Assays which are performed in cell-free systems, such as can be derived with purified or semi-purified proteins, are often preferred as "primary" screens in that they can be generated to permit rapid development and relatively easy detection of an alteration in a molecular target which is mediated by an analyte. Moreover, the effects of cellular toxicity and/or bioavailability of the analyte can be generally ignored in the in vitro system, the assay instead being focused primarily on the effect of the analyte on the molecular target as may be manifest in an alteration of binding affinity with upstream or downstream elements. Accordingly, in an exemplary screening method of the present invention, an analyte is contacted with rhNur77 or Nur77 binding partner. The rhNur77 or Nur77 binding partner can be soluble, on a membrane surface, or immobilized on a solid substrate such as the surface of the wells of microtiter plate, bioassay chip, or the like. To the mixture of the analyte and the rhNur77 or Nur77 binding partner is then added a composition containing Nur77 binding partner or rhNur77 protein, respectively. Detection and quantification of complexes of rhNur77 and RXR in the presence of the analyte provide a means for determining an analyte's efficacy at inhibiting or potentiating complex formation between rhNur77 and Nur77 binding partner. The efficacy of the analyte can be assessed by generating dose response curves from data obtained using various concentrations of the test compound. Moreover, a control can also be performed to provide a baseline for comparison. For the control, isolated and purified rhNur77 or Nur77 binding partner is added to a composition containing the Nur77 binding partner or rhNur77 and the formation of a rhNur77/Nur77 binding partner complex is quantified in the absence of the analyte.

In one aspect, high throughput screening methods involve providing a library containing a large number of potential Nur77 modulators (candidate compounds). Such "combinatorial chemical libraries" are then screened in one or more assays, to identify those library member's particular chemical species or subclasses that display a desired characteristic activity. The compounds thus identified can serve as conventional "lead compounds" or can themselves be used as potential Nur77 modulators.

Devices for the preparation of combinatorial libraries are commercially available (See, for example, 357 MPS, 390 MPS, Advanced Chem Tech, Louisville, Ky.; Symphony, Rainin, Woburn, Mass.; 433A Applied Biosystems, Foster City, Calif.; 9050 Plus, Millipore, Bedford, Mass.). A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (See, for example, ComGenex, Princeton, N.J.; Asinex, Moscow, Russia; Tripos, Inc., St. Louis, Mo.; ChemStar, Ltd, Moscow, Russia; 3D Pharmaceuticals, Exton, Pa.; Martek Biosciences, Columbia, Md.).

Any of the assays described herein are amenable to high throughput screening. As described above, the analytes are preferably screened by the methods disclosed herein. High throughput systems for such screening are well known to those of skill in the art. For example, U.S. Pat. No. 5,559,410 discloses high throughput screening methods for protein binding and U.S. Pat. Nos. 5,576,220 and 5,541,061 disclose high throughput methods of screening for ligand/antibody binding.

In addition, high throughput screening systems are commercially available (See, for example, Zymark Corp., Hopkinton, Mass.; Air Technical Industries, Mentor, Ohio; Beckman Instruments, Inc. Fullerton, Calif.; Precision Systems, Inc., Natick, Mass.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols. Thus, for example, Zymark Corp. provides technical bulletins describing screening systems for detecting the modulation of gene transcription, ligand binding, and the like.

The following examples are intended to promote a further understanding of the present invention.

EXAMPLE 1

By aligning the nucleotide sequences of the dog, mouse, rat, and human Nur77, we identified significant identity in the nucleotide sequences encoding the Nur77s. PCR primers for amplifying the entire coding region of the RhNur77 were designed based upon the nucleotide sequences at the ends of the coding region for the human Nur77. Forward PCR primer had the nucleotide sequence 5'-ATGCC CTGTA TCCAA GCCCA ATAT-3' (SEQ ID NO:5) and the reverse PCR primer had the nucleotide sequence 5'TCAGA AGGGC AGCGT GTCCA T-3 (SEQ ID NO:6).

RNA was extracted from Rhesus monkey prostrate tissue using the TRIZOL method available from Life Technologies (Invitrogen, La Jolla, Calif.). The RNA was used to prepare cDNA using SUPERSCRIPT II (Invitrogen). A mixture containing 1 µg RNA, 0.5 µg Oligo(dT)12, and 1 µL of 10 mM dNTP in a final volume of about 12 µL was prepared. The mixture was heated at 65° C. for five minutes and then chilled on ice. To the chilled mixture was added 4 µL of 5× First Strand Buffer (Invitrogen), 2 µL 0.1 M DTT, and 1 µL (40 units) RNase OUT. The mixture was incubated at 42° C. for two minutes before adding 1 µL (200 units) SUPERSCRIPT II reverse transcriptase and incubating for 50 minutes at 42° C. to make the cDNA. Afterwards, the mixture was heated to 70° C. for 15 minutes. RNA was removed by adding 1 µL (2 units) of *E. coli* RNase H and incubating the mixture for 20 minutes at 37° C. The mixture containing the cDNA was stored at −20° C. until ready for use.

RhNur77 was PCR amplified from the cDNA using the EXPAND HIGH FIDELITY PCR system from Roche Applied Science (Indianapolis, Ind.) as follows. A mixture containing 2.5 µL of 10 mM dNTP, 2.5 µL of 100 pmol/µL forward primer, and 2.5 µL of reverse primer in water to a final volume of 60 µL was prepared. To 24 µL of the mixture was added 1 µL of the above cDNA. A mixture containing 48.13 µL water, 2.5 µL 10× PCR buffer with MgCl, and 3.75 µL of enzyme was prepared and 25 µL of the mixture was added to the 25 µL mixture containing the cDNA. The final concentration of constituents was 0.2 mM dNTP, 2 pmol forward primer, 2 pmol reverse primer, about 0.23×PCR buffer with MgCl. The PCR reaction was performed as follows: one cycle of 94° C. for five minutes, 55° C. for 30 seconds, and two minutes, five seconds at 72° C.; 28 cycles of 94° C. for 30 seconds, 55° C. for 30 seconds, and two minutes, five seconds at 72° C.; and, one cycle of 94° C. for five minutes, 55° C. for 30 seconds, and seven minutes at 72° C. Afterwards, 1 µL of Taq polymerase was added to the reaction mixture and the reaction continued at 72° C. for 30 minutes.

The PCR amplification products were resolved by electrophoresis on a 1% agarose gel and DNA migrating at the position expected for DNA of about 1.8 kb was eluted from the gel using the QIAQUICK Gel extraction Kit (Qiagen, Valencia, Calif.) and ligated into the pCR2.1 TA CLONING vector (Invitrogen). Potentially positive colonies were picked and checked for RhNur77 by using the above forward and reverse primers. Clones identified as containing the RhNur77 were prepared for sequencing using the primers shown in Table 1.

TABLE 1

| Name | Sequence | SEQ ID NO: |
|---|---|---|
| M13 rvr | 5'-CAGGA AACAG CTATG AC-3' | 7 |
| M13 rvr2 | 5'-GGCTC GTATGT TGTGT GGAA-3' | 8 |
| M13 fwd | 5'-GTAAA ACGAC GGCCA G-3' | 9 |
| Nur77 fwd2 | 5'-AAGCC CACCA TGGAC CTGGC CAG-3' | 10 |
| Nur77 fwd3 | 5'-AGCCA GACTT ACGAA GGCC-3' | 11 |
| Nur77 fwd4 | 5'-CCAAG TACAT CTGCC TGG-3' | 12 |

TABLE 1-continued

| Name | Sequence | SEQ ID NO: |
|---|---|---|
| Nur77 fwd5 | 5'-GGACT ACTCC AAGTT CCAGG-3' | 13 |
| Nur77 fwd6 | 5'-CCTGC CTTCG CCTGC C-3' | 14 |
| Nur77 rvr2 | 5'-ACTGT GCGCT TGAAG AAGCC-3' | 15 |
| Nur77 rvr3 | 5'-AGACG TGCTC CTTCA GGCAG C-3' | 16 |
| Nur77 rvr4 | 5'-CACGT CCCCG GCATC TTCCT T-3' | 17 |
| Nur77 rvr5 | 5'-TCTGT CCGGA CAACT TCCTT C-3' | 18 |
| Nur77 rvr6 | 5'-TGGGC AGTTG CTCTG TCCAT G-3' | 19 |

The consensus sequence of the RhNur77 was determined from the sequencing data. The data was verified by three separate sequencing experiments using the primers of Table 1. Two clones 20 were identified that had identical nucleotide sequences except for the nucleotide at position 1435 which can be either a T or a C, clone 1 or 2, respectively. Depending on whether the nucleotide is a C or a T, the amino acid sequence of the rhNur77 contains a phenylalanine or leucine, respectively, at position 479. The nucleotide sequence of the clone 1 rhNur77 is shown in FIG. 1 and its encoded amino acid sequence is shown in FIG. 2. The clone 1 rhNur77 nucleotide sequence has a nucleotide sequence of about 89.9% identity to the nucleotide sequence of the human Nur77 (FIG. 4) and its encoded RhNur77 has an amino acid sequence of about 95.8% identity to the amino acid sequence of the human Nur77 (FIG. 3).

EXAMPLE 2

A nucleic acid encoding a chimeric nuclear receptor comprising the rat glucocorticoid receptor (GR) DBD fused to the rhNur77 LBD is constructed and the nucleic acid inserted downstream of the SV40 promoter in plasmid pSG5. The rat GR DBD consists of about amino acid 1 to about amino acid 505 and the rhNur77 LBD (and AF2) consists of the amino acid sequence beginning from about amino acid 333 to about amino acid 599 (See FIG. 2). A nucleic acid encoding the rat GR DBD, which consists of nucleotides 1 to 1583 (and which includes the proximal 5' untranslated sequences), is ligated to the nucleic encoding the rhNur77 (nucleotides 997 to 1797). At the junction in the fusion protein between amino acid 505 of the rat GR DBD and amino acid 333 of the rhNur77 LDB there are three extra amino acids, Alanine, Arginine, and Glutamic acid, which are encoded by the oligonucleotide 5'-GCTCGAGAA-3' (SEQ ID NO:20) which includes an XhoI restriction enzyme site.

The chimeric nuclear receptor is constructed by ligating the rat GRDBD encoding nucleotide fragment (nucleotides 1 to 1583) to the rhNur77 LBD encoding nucleotide fragment (nucleotides 997 to 1797) and then inserting the ligated GRDBD/rhNur77 LBD nucleotide fragments into the pSG5 plasmid expression vector between the EcoRI and BamH1 sites.

A reporter gene expression cassette comprising the MMTV(2xGRE) promoter is constructed as described in Schmidt et al., Mol. Endocrinol. 6(10):1634-41 (1992).

EXAMPLE 3

A routine transient transfection assay for identifying agonists of rhNur77 activity is described. While the transfection uses the FuGENE6 method of Roche Applied Science, Indianapolis, Ind., other transfection methods can be used.

In general, the method consists of plating about 0.8 to $1\times10^4$ transfected COS-1 or CHO cells per well of 96-well tissue culture plates that are UV and visible light transparent. The media that the cells are plated in is exponential growth medium, which consists of phenol red-free DMEM containing 10% fetal bovine serum and 1× penicillin/streptomycin. Incubation conditions are 37° C. and 5% $CO_2$. The transfection is done in batch mode.

For a transfection, the cells are trypsinized and resuspended to about $8\times10^4$ cells/mL in fresh medium. FuGENE6 is mixed with serum-free medium (for example, OPTIMEM, Invitrogen, Carlsbad, Calif.) at a ratio of 2 to 3. About 0.625 ng of DNA encoding the chimeric receptor of Example 2 and 0.625 ng DNA comprising the MMTV promoter operably linked to the luciferase gene (MMTV-LUC) are added to the FuGENE6 in serum-free medium and the mixture incubated at room temperature for about 20 minutes. The mixture is then added to one mL of the cell suspension and 100 µL aliquots plated to the wells of a 96-well tissue culture plate. Thus, a total ten wells contain cells, each containing about 8,000 cells. About 16 to 24 hours after transfection, for each well, about 1 uL of an analyte in a vehicle such as DMSO is added to the well. At least one well is reserved as a control and receives the vehicle alone. After 24 hours exposure to the analytes, the cells are assayed for luciferase activity. The cells are lysed by a Promega cell culture lysis buffer for approximately 30 min and then the luciferase activity in the extracts is assayed in the 96-well format liminometer (MICROBETA JET 1450, Perkin Elmer, Boston, Mass.). Results are calculated as fold induction of compound treated cells over control treated cells.

EXAMPLE 4

This example describes a method for making polyclonal antibodies specific for rhNur77.

Antibodies are generated in New Zealand white rabbits over a 10-week period. Purified rhNur77 is emulsified by mixing with an equal volume of Freund's complete adjuvant and injected into three subcutaneous dorsal sites for a total of 0.1 mg rhNur77 per immunization. A booster containing about 0.1 mg rhNur77 emulsified in an equal volume of Freund's incomplete adjuvant is administered subcutaneously two weeks later. Animals are bled from the articular artery. The blood is allowed to clot and the serum collected by centrifugation. The serum is stored at −20° C.

For purification, rhNur77 is immobilized on an activated support. Antisera is passed through the sera column and then washed. Specific antibodies are eluted via a pH gradient, collected, and stored in a borate buffer (0.125 M total borate) at −0.25 mg/mL. The anti-rhNur77 antibody titers are determined using ELISA methodology with free rhNur77 bound in solid phase (1 pg/well). Detection is obtained using biotinylated anti-rabbit IgG, HRP-SA conjugate, and ABTS.

EXAMPLE 5

This example describes a method for making monoclonal antibodies specific for rhNur77.

BALB/c mice are immunized with an initial injection of about 1 µg of purified rhNur77 per mouse mixed 1:1 with Freund's complete adjuvant. After two weeks, a booster injection of about 1 µg of the antigen is injected into each mouse intravenously without adjuvant. Three days after the booster injection serum from each of the mice is checked for antibodies specific for the rhNur77.

The spleens are removed from mice positive for antibodies specific for rhNur77 and washed three times with serum-free DMEM and placed in a sterile Petri dish containing about 20 mL of DMEM containing 20% fetal bovine serum, 1 mM pyruvate, 100 units penicillin, and 100 units streptomycin. The cells are released by perfusion with a 23 gauge needle. Afterwards, the cells are pelleted by low-speed centrifugation and the cell pellet is resuspended in 5 mL 0.17 M ammonium chloride and placed on ice for several minutes. Then 5 mL of 20% bovine fetal serum is added and the cells pelleted by low-speed centrifugation. The cells are then resuspended in 10 mL DMEM and mixed with mid-log phase myeloma cells in serum-free DMEM to give a ratio of 3:1. The cell mixture is pelleted by low-speed centrifugation, the supernatant fraction removed, and the pellet allowed to stand for 5 minutes. Next, over a period of 1 minute, 1 mL of 50% polyethylene glycol (PEG) in 0.01 M HEPES, pH 8.1, at 37° C. is added. After 1 minute incubation at 37° C., 1 mL of DMEM is added for a period of another 1 minute, then a third addition of DMEM is added for a further period of 1 minute. Finally, 10 mL of DMEM is added over a period of 2 minutes. Afterwards, the cells are pelleted by low-speed centrifugation and the pellet resuspended in DMEM containing 20% fetal bovine serum, 0.016 mM thymidine, 0.1 hypoxanthine, 0.5 µM aminopterin, and 10% hybridoma cloning factor (HAT medium). The cells are then plated into 96-well plates.

After 3, 5, and 7 days, half the medium in the plates is removed and replaced with fresh HAT medium. After 11 days, the hybridoma cell supernatant is screened by an ELISA assay. In this assay, 96-well plates are coated with the rhNur77. One hundred µL of supernatant from each well is added to a corresponding well on a screening plate and incubated for 1 hour at room temperature. After incubation, each well is washed three times with water and 100 µL of a horseradish peroxide conjugate of goat anti-mouse IgG (H+L), A, M (1:1,500 dilution) is added to each well and incubated for 1 hour at room temperature. Afterwards, the wells are washed three times with water and the substrate OPD/hydrogen peroxide is added and the reaction is allowed to proceed for about 15 minutes at room temperature. Then 100 µL of 1 M HCl is added to stop the reaction and the absorbance of the wells is measured at 490 nm. Cultures that have an absorbance greater than the control wells are removed to two $cm^2$ culture dishes, with the addition of normal mouse spleen cells in HAT medium. After a further three days, the cultures are re-screened as above and those that are positive are cloned by limiting dilution. The cells in each two $cm^2$ culture dish are counted and the cell concentration adjusted to $1 \times 10^5$ cells per mL. The cells are diluted in complete medium and normal mouse spleen cells are added. The cells are plated in 96-well plates for each dilution. After 10 days, the cells are screened for growth. The growth positive wells are screened for antibody production; those testing positive are expanded to 2 $cm^2$ cultures and provided with normal mouse spleen cells. This cloning procedure is repeated until stable antibody producing hybridomas are obtained. The stable hybridomas are progressively expanded to larger culture dishes to provide stocks of the cells.

Production of ascites fluid is performed by injecting intraperitoneally 0.5 mL of pristane into female mice to prime the mice for ascites production. After 10 to 60 days, $4.5 \times 10^6$ cells are injected intraperitoneally into each mouse and ascites fluid is harvested between 7 and 14 days later.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. An isolated nucleic acid comprising the nucleotide sequence encoding a rhesus monkey Nur77 polypeptide having the amino acid sequence set forth in SEQ ID NO:2.

2. The isolated nucleic acid of claim 1, wherein the nucleic acid comprises nucleotides having the nucleotide sequence set forth in SEQ ID NO: 1.

3. A vector comprising the nucleic acid of claim 1 operably linked to a heterologous promoter.

4. An isolated cell comprising the vector of claim 3.

5. A method for producing a rhesus monkey Nur77 (rhNur77) polypeptide comprising:
    (a) providing the cell of claim 4; and
    (b) culturing the cell under conditions to produce the rhNur77 polypeptide.

6. An isolated nucleic acid comprising:
    (a) nucleotides having the sequence set forth in SEQ ID NO:1 wherein nucleotide 1435 is a cytosine;
    (b) nucleotides encoding a polypeptide comprising amino acids 1 to 598 of SEQ ID NO:2;
    (c) nucleotides encoding a polypeptide comprising amino acids 332 to 566 of SEQ ID NO:2 which retains the function of the ligand binding domain (LBD) of Nur77;
    (d) nucleotides encoding a polypeptide comprising amino acids having the sequence set forth in SEQ ID NO:2 wherein amino acid 479 is a leucine.

7. A vector comprising the nucleic acid of claim 6 operably linked to a heterologous promoter.

8. An isolated cell comprising the vector of claim 7.

9. A method for producing a rhesus monkey Nur77 (rhNur77) polypeptide comprising:
    (a) providing the cell of claim 8; and
    (b) culturing the cell under conditions to produce the rhNur77 polypeptide.

10. An isolated nucleic acid consisting of:
    (a) nucleotides 997 to 1698 of SEQ ID NO:1; or
    (b) nucleotides 800 to 996 of SEQ ID NO:1.

11. A vector comprising the nucleic acid of claim 10 operably linked to a heterologous promoter.

12. A cell comprising the vector of claim 11.

13. An isolated method for producing a rhesus monkey Nur77 (rhNur77) polypeptide comprising:
    (a) providing the cell of claim 12; and
    (b) culturing the cell under conditions to produce the rhNur77 polypeptide.

* * * * *

SEQUENCE LISTING

```
<160> NUMBER OF SEQ ID NOS: 20

<210> SEQ ID NO 1
<211> LENGTH: 1797
<212> TYPE: DNA
<213> ORGANISM: Macaca mulatta

<400> SEQUENCE: 1
atgccctgta tccaagccca atatgggaca ccagcaccaa gcccaggacc ccgagaccac        60
ctggcaagcg acccctgac ccccgagctc agcaagccca ccatggacct ggccagccct       120
gaggcagccc ccaccgcccc cacggccctg cccagcttca gcactttcat ggacggctac       180 acggggagt ttgacaccctt cctgtaccag ctgccgggaa cggcccagcc atgctcttcg       240
gcctcctctt cggcctcctc cacgtcctcc tcctcggcca cctcccccgc ctctgcttcc       300
ttcaagtttg aggacttcca ggtgtacggc tgctaccctg gccccctgag cggtcccctg       360
gacgagaccc tgtcctccag cggttccgac tactacggca gccccctgct cagcgccgtcc      420
```

```
ccgtccacgc ccagcttcca gccacccag ctctctccct gggatggctc gttcggcccc    480
ttctcaccca gccagacgta cgaaggcctg cgggcatgga cagagcaact gcccaaggct    540
tctgggcacc cccagccgcc tgcctttttt tccttcagcc ccctactgg tcccagtccc     600
agccttgccc agagccccctt gaagctgttc ccctcacagg ccacctgcca gctggggggag  660
agagaaagtt attccatatc cacggctttc cgggcctgg cgcccacttc tccacacctc     720
gacggcccag ggatgctgga cgcaccggtg ccttcggcca aggcccggag cggggccccc    780
agtggaagcg agggccgctg tgccgtgtgt ggggacaacg cttcgtgcca gcattacggc    840
gtccgcacct gcgagggctg taagggcttc ttcaagcgca cagtacagaa aaacgccaag    900
tacatctgcc tggctaacaa ggactgcccc gtggacaaga ggcggcgaaa ccgctgccag    960
ttctgtcgct tccagaagtg cctggccgta ggcatggtga aggaagttgt ccggacagac    1020
agcctgaagg ggcggcgggg tcggctccct tcgaagccca gcagccccc ggacgcctcc     1080
cctgccaacc tcctcacgtc cctggtcagg gcacacctgg actccgggcc cagcacagcc    1140
aaactggact actccaagtt ccaggagctg gtactgcccc acttcgggaa ggaagatgcc    1200
ggggacgtgc agcagttcta cgacctgctt tcgggttccc tggaggtcat ccgcaagtgg    1260
gccgagaaga tccccggctt tgccgagctg tccccgggtg accaggacct gctgctggag    1320
tcggccttcc tggagctctt catcctccgc ctggcctacc gctcgaagcc ggccgagggg   1380
aagctcatct tctgctcggg cctggtgctc accggctgc agtgcgcccg cggctttggc     1440
gactggatcg acagcattct ggccttctct cggtccctgc acggcctggt ggtggacgtc    1500
cctgccttcg cctgcctctc ggcgctcgtc ctcatcacag accggcacgg gctgcaagag    1560
ccaaggcggg tggaggagct gcaaaatcgc atcgccagct gcctgaagga gcacgtctcg    1620
gccgtggcgg gcgaaccgca gccggccagc tgcctgtcac gcctgctggg caagctcccc    1680
gagctgcgga ccctgtgcac ccagggcttg caacgcatct tctacctcaa gctggaggac    1740
ttggtgcccc ctccgcccat tgtcgacaag atctttatgg acacgctgcc cttctga       1797
```

<210> SEQ ID NO 2
<211> LENGTH: 598
<212> TYPE: PRT
<213> ORGANISM: Macaca mulatta

<400> SEQUENCE: 2

```
Met Pro Cys Ile Gln Ala Gln Tyr Gly Thr Pro Ala Pro Ser Pro Gly
 1               5                   10                  15

Pro Arg Asp His Leu Ala Ser Asp Pro Leu Thr Pro Glu Leu Ser Lys
             20                  25                  30

Pro Thr Met Asp Leu Ala Ser Pro Glu Ala Ala Pro Thr Ala Pro Thr
         35                  40                  45

Ala Leu Pro Ser Phe Ser Thr Phe Met Asp Gly Tyr Thr Gly Glu Phe
     50                  55                  60

Asp Thr Phe Leu Tyr Gln Leu Pro Gly Thr Ala Gln Pro Cys Ser Ser
 65                  70                  75                  80

Ala Ser Ser Ser Ala Ser Ser Thr Ser Ser Ser Ala Thr Ser Pro
             85                  90                  95

Ala Ser Ala Ser Phe Lys Phe Glu Asp Phe Gln Val Tyr Gly Cys Tyr
            100                 105                 110

Pro Gly Pro Leu Ser Gly Pro Leu Asp Glu Thr Leu Ser Ser Ser Gly
        115                 120                 125
```

```
Ser Asp Tyr Tyr Gly Ser Pro Cys Ser Ala Pro Ser Pro Ser Thr Pro
130                 135                 140

Ser Phe Gln Pro Pro Gln Leu Ser Pro Trp Asp Gly Ser Phe Gly Pro
145                 150                 155                 160

Phe Ser Pro Ser Gln Thr Tyr Glu Gly Leu Arg Ala Trp Thr Glu Gln
                165                 170                 175

Leu Pro Lys Ala Ser Gly His Pro Gln Pro Ala Phe Phe Ser Phe
            180                 185                 190

Ser Pro Pro Thr Gly Pro Ser Pro Ser Leu Ala Gln Ser Pro Leu Lys
            195                 200                 205

Leu Phe Pro Ser Gln Ala Thr Cys Gln Leu Gly Glu Gly Glu Ser Tyr
210                 215                 220

Ser Ile Ser Thr Ala Phe Pro Gly Leu Ala Pro Thr Ser Pro His Leu
225                 230                 235                 240

Asp Gly Pro Gly Met Leu Asp Ala Pro Val Thr Ser Thr Lys Ala Arg
            245                 250                 255

Ser Gly Ala Pro Ser Gly Ser Glu Gly Arg Cys Ala Val Cys Gly Asp
            260                 265                 270

Asn Ala Ser Cys Gln His Tyr Gly Val Arg Thr Cys Glu Gly Cys Lys
            275                 280                 285

Gly Phe Phe Lys Arg Thr Val Gln Lys Asn Ala Lys Tyr Ile Cys Leu
            290                 295                 300

Ala Asn Lys Asp Cys Pro Val Asp Lys Arg Arg Arg Asn Arg Cys Gln
305                 310                 315                 320

Phe Cys Arg Phe Gln Lys Cys Leu Ala Val Gly Met Val Lys Glu Val
                325                 330                 335

Val Arg Thr Asp Ser Leu Lys Gly Arg Arg Gly Arg Leu Pro Ser Lys
            340                 345                 350

Pro Lys Gln Pro Pro Asp Ala Ser Pro Ala Asn Leu Leu Thr Ser Leu
            355                 360                 365

Val Arg Ala His Leu Asp Ser Gly Pro Ser Thr Ala Lys Leu Asp Tyr
370                 375                 380

Ser Lys Phe Gln Glu Leu Val Leu Pro His Phe Gly Lys Glu Asp Ala
385                 390                 395                 400

Gly Asp Val Gln Gln Phe Tyr Asp Leu Leu Ser Gly Ser Leu Glu Val
                405                 410                 415

Ile Arg Lys Trp Ala Glu Lys Ile Pro Gly Phe Ala Glu Leu Ser Pro
            420                 425                 430

Gly Asp Gln Asp Leu Leu Leu Glu Ser Ala Phe Leu Glu Leu Phe Ile
            435                 440                 445

Leu Arg Leu Ala Tyr Arg Ser Lys Pro Ala Glu Gly Lys Leu Ile Phe
450                 455                 460

Cys Ser Gly Leu Val Leu His Arg Leu Gln Cys Ala Arg Gly Phe Gly
465                 470                 475                 480

Asp Trp Ile Asp Ser Ile Leu Ala Phe Ser Arg Ser Leu His Ser Leu
                485                 490                 495

Val Val Asp Val Pro Ala Phe Ala Cys Leu Ser Ala Leu Val Leu Ile
            500                 505                 510

Thr Asp Arg His Gly Leu Gln Glu Pro Arg Arg Val Glu Glu Leu Gln
            515                 520                 525

Asn Arg Ile Ala Ser Cys Leu Lys Glu His Val Ser Ala Val Ala Gly
530                 535                 540

Glu Pro Gln Pro Ala Ser Cys Leu Ser Arg Leu Leu Gly Lys Leu Pro
```

-continued

```
                545                 550                 555                 560
Glu Leu Arg Thr Leu Cys Thr Gln Gly Leu Gln Arg Ile Phe Tyr Leu
                    565                 570                 575
Lys Leu Glu Asp Leu Val Pro Pro Pro Ile Val Asp Lys Ile Phe
                580                 585                 590
Met Asp Thr Leu Pro Phe
        595

<210> SEQ ID NO 3
<211> LENGTH: 1797
<212> TYPE: DNA
<213> ORGANISM: Homo Sapien

<400> SEQUENCE: 3
atgccctgta tccaagccca atatgggaca ccagcaccga gtccgggacc ccgtgaccac       60
ctggcaagcg accccctgac ccctgagttc atcaagccca ccatggacct ggccagcccc      120
gaggcagccc ccgctgcccc cactgccctg cccagcttca gccttcat ggacggctac        180
acaggagagt ttgacacctt cctctaccag ctgccaggaa cagtccagcc atgctcctca      240
gcctcctcct cggcctcctc cacatcctcg tcctcagcca cctcccctgc ctctgcttcc      300
ttcaagttcg aggacttcca ggtgtacggc tgctaccccg cccctgag cggcccagtg        360
gatgaggccc tgtcctccag tggctctgac tactatggca cccctgctc ggccccgtcg       420
ccctccacgc ccagcttcca gccgcccag ctctctccct gggatggctc cttcggccac       480
ttctcgccca gccagactta cgaaggcctg cgggcatgga cagagcagct gcccaaagcc      540
tctgggcccc cacagcctcc agccttctttt ccttcagtc ctcccaccgg ccccagcccc      600
agcctggccc agagccccct gaagttgttc ccctcacagg ccacccacca gctgggggag     660
ggagagagct attccatgcc tacggccttc ccaggttggg cacccacttc tccacacctt      720
gagggctcgg ggatactgga tacacccgtg acctcaacca aggcccggag cggggccca       780
ggtggaagtg aaggccgctg tgctgtgtgt ggggacaacg cttcatgcca gcattatggt      840
gtccgcacat gtgagggctg caagggcttc ttcaagcgca cagtgcagaa aaacgccaag      900
tacatctgcc tggctaacaa ggactgccct gtggacaaga ggcggcgaaa ccgctgccag      960
ttctgccgct tccagaagtg cctggcggtg ggcatggtga aggaagttgt ccgaacagac     1020
agcctgaagg ggcggcgggg ccggctacct tcaaaaccca gcagccccc agatgcctcc      1080
cctgccaatc tcctcactt cctggtccgt gcacacctgg actcagggcc cagcactgcc      1140
aaactggact actccaagtt ccaggagctg gtgctgcccc actttgggaa ggaagatgct     1200
ggggatgtac agcagttcta cgacctgctc tccggttctc tggaggtcat ccgcaagtgg    1260
gcggagaaga tccctggctt tgctgagctg tcaccggctg accaggacct gttgctggag    1320
tcggccttcc tggagctctt catcctccgc ctggcgtaca ggctaagcc aggcgagggc    1380
aagctcatct tctgctcagg cctggtgcta caccggctgc agtgtgcccg tggcttcggg    1440
gactggattg acagtatcct ggccttctca aggtccctgc acagcttgct tgtcgatgtc    1500
cctgccttcg cctgcctctc tgcccttgtc ctcatcaccg accggcatgg gctgcaggag    1560
ccgcggcggg tggaggagct gcagaaccgc atcgccagct gcctgaagga gcacgtggca    1620
gctgtggcgg gcgagcccca gccagccagc tgcctgtcac gtctgttggg caaactgccc    1680
gagctgcgga ccctgtgcac ccagggcctg cagcgcatct ctacctcaa gctggaggac    1740
ttggtgcccc ctccacccat cattgacaag atcttcatgg acacgctgcc cttctga      1797
```

<210> SEQ ID NO 4
<211> LENGTH: 598
<212> TYPE: PRT
<213> ORGANISM: Homo Sapien

<400> SEQUENCE: 4

```
Met Pro Cys Ile Gln Ala Gln Tyr Gly Thr Pro Ala Pro Ser Pro Gly
 1               5                  10                  15

Pro Arg Asp His Leu Ala Ser Asp Pro Leu Thr Pro Glu Phe Ile Lys
                20                  25                  30

Pro Thr Met Asp Leu Ala Ser Pro Glu Ala Ala Pro Ala Ala Pro Thr
            35                  40                  45

Ala Leu Pro Ser Phe Ser Thr Phe Met Asp Gly Tyr Thr Gly Glu Phe
        50                  55                  60

Asp Thr Phe Leu Tyr Gln Leu Pro Gly Thr Val Gln Pro Cys Ser Ser
 65                 70                  75                  80

Ala Ser Ser Ser Ala Ser Ser Thr Ser Ser Ser Ala Thr Ser Pro
                85                  90                  95

Ala Ser Ala Ser Phe Lys Phe Glu Asp Phe Gln Val Tyr Gly Cys Tyr
                100                 105                 110

Pro Gly Pro Leu Ser Gly Pro Val Asp Glu Ala Leu Ser Ser Ser Gly
                115                 120                 125

Ser Asp Tyr Tyr Gly Ser Pro Cys Ser Ala Pro Ser Pro Ser Thr Pro
            130                 135                 140

Ser Phe Gln Pro Pro Gln Leu Ser Pro Trp Asp Gly Ser Phe Gly His
145                 150                 155                 160

Phe Ser Pro Ser Gln Thr Tyr Glu Gly Leu Arg Ala Trp Thr Glu Gln
                165                 170                 175

Leu Pro Lys Ala Ser Gly Pro Pro Gln Pro Pro Ala Phe Phe Ser Phe
                180                 185                 190

Ser Pro Pro Thr Gly Pro Ser Pro Ser Leu Ala Gln Ser Pro Leu Lys
            195                 200                 205

Leu Phe Pro Ser Gln Ala Thr His Gln Leu Gly Glu Gly Glu Ser Tyr
            210                 215                 220

Ser Met Pro Thr Ala Phe Pro Gly Leu Ala Pro Thr Ser Pro His Leu
225                 230                 235                 240

Glu Gly Ser Gly Ile Leu Asp Thr Pro Val Thr Ser Thr Lys Ala Arg
                245                 250                 255

Ser Gly Ala Pro Gly Gly Ser Glu Gly Arg Cys Ala Val Cys Gly Asp
                260                 265                 270

Asn Ala Ser Cys Gln His Tyr Gly Val Arg Thr Cys Glu Gly Cys Lys
            275                 280                 285

Gly Phe Phe Lys Arg Thr Val Gln Lys Asn Ala Lys Tyr Ile Cys Leu
        290                 295                 300

Ala Asn Lys Asp Cys Pro Val Asp Lys Arg Arg Arg Asn Arg Cys Gln
305                 310                 315                 320

Phe Cys Arg Phe Gln Lys Cys Leu Ala Val Gly Met Val Lys Glu Val
                325                 330                 335

Val Arg Thr Asp Ser Leu Lys Gly Arg Arg Gly Arg Leu Pro Ser Lys
            340                 345                 350

Pro Lys Gln Pro Pro Asp Ala Ser Pro Ala Asn Leu Leu Thr Ser Leu
        355                 360                 365

Val Arg Ala His Leu Asp Ser Gly Pro Ser Thr Ala Lys Leu Asp Tyr
        370                 375                 380
```

```
Ser Lys Phe Gln Glu Leu Val Leu Pro His Phe Gly Lys Glu Asp Ala
385                 390                 395                 400

Gly Asp Val Gln Gln Phe Tyr Asp Leu Leu Ser Gly Ser Leu Glu Val
            405                 410                 415

Ile Arg Lys Trp Ala Glu Lys Ile Pro Gly Phe Ala Glu Leu Ser Pro
        420                 425                 430

Ala Asp Gln Asp Leu Leu Leu Glu Ser Ala Phe Leu Glu Leu Phe Ile
            435                 440                 445

Leu Arg Leu Ala Tyr Arg Ser Lys Pro Gly Glu Gly Lys Leu Ile Phe
    450                 455                 460

Cys Ser Gly Leu Val Leu His Arg Leu Gln Cys Ala Arg Gly Phe Gly
465                 470                 475                 480

Asp Trp Ile Asp Ser Ile Leu Ala Phe Ser Arg Ser Leu His Ser Leu
                485                 490                 495

Leu Val Asp Val Pro Ala Phe Ala Cys Leu Ser Ala Leu Val Leu Ile
            500                 505                 510

Thr Asp Arg His Gly Leu Gln Glu Pro Arg Arg Val Glu Glu Leu Gln
    515                 520                 525

Asn Arg Ile Ala Ser Cys Leu Lys Glu His Val Ala Ala Val Ala Gly
    530                 535                 540

Glu Pro Gln Pro Ala Ser Cys Leu Ser Arg Leu Leu Gly Lys Leu Pro
545                 550                 555                 560

Glu Leu Arg Thr Leu Cys Thr Gln Gly Leu Gln Arg Ile Phe Tyr Leu
            565                 570                 575

Lys Leu Glu Asp Leu Val Pro Pro Pro Ile Ile Asp Lys Ile Phe
            580                 585                 590

Met Asp Thr Leu Pro Phe
        595

<210> SEQ ID NO 5
<211> LENGTH: 24
<212> TYPE: DNA
<213> ORGANISM: Artificial Sequence
<220> FEATURE:
<223> OTHER INFORMATION: PCT Forward Primer

<400> SEQUENCE: 5
atgccctgta tccaagccca atat                                      24

<210> SEQ ID NO 6
<211> LENGTH: 21
<212> TYPE: DNA
<213> ORGANISM: Artificial Sequence
<220> FEATURE:
<223> OTHER INFORMATION: PCT Reverse Primer

<400> SEQUENCE: 6
tcagaagggc agcgtgtcca t                                         21

<210> SEQ ID NO 7
<211> LENGTH: 17
<212> TYPE: DNA
<213> ORGANISM: Artificial Sequence
<220> FEATURE:
<223> OTHER INFORMATION: M13 rvr primer

<400> SEQUENCE: 7
caggaaacag ctatgac                                              17
```

<210> SEQ ID NO 8
<211> LENGTH: 20
<212> TYPE: DNA
<213> ORGANISM: Artificial Sequence
<220> FEATURE:
<223> OTHER INFORMATION: M13 rvr2 primer

<400> SEQUENCE: 8
ggctcgtatg ttgtgtggaa                                               20

<210> SEQ ID NO 9
<211> LENGTH: 16
<212> TYPE: DNA
<213> ORGANISM: Artificial Sequence
<220> FEATURE:
<223> OTHER INFORMATION: M13 fwd primer

<400> SEQUENCE: 9
gtaaaacgac ggccag                                                   16

<210> SEQ ID NO 10
<211> LENGTH: 23
<212> TYPE: DNA
<213> ORGANISM: Artificial Sequence
<220> FEATURE:
<223> OTHER INFORMATION: Nur77 fwd2 primer

<400> SEQUENCE: 10
aagcccacca tggacctggc cag                                           23

<210> SEQ ID NO 11
<211> LENGTH: 19
<212> TYPE: DNA
<213> ORGANISM: Artificial Sequence
<220> FEATURE:
<223> OTHER INFORMATION: Nur77 fwd3 primer

<400> SEQUENCE: 11
agccagactt acgaaggcc                                                19

<210> SEQ ID NO 12
<211> LENGTH: 18
<212> TYPE: DNA
<213> ORGANISM: Artificial Sequence
<220> FEATURE:
<223> OTHER INFORMATION: Nur77 fwd4 primer

<400> SEQUENCE: 12
ccaagtacat ctgcctgg                                                 18

<210> SEQ ID NO 13
<211> LENGTH: 20
<212> TYPE: DNA
<213> ORGANISM: Artificial Sequence
<220> FEATURE:
<223> OTHER INFORMATION: Nur77 fwd5 primer

<400> SEQUENCE: 13
ggactactcc aagttccagg                                               20

<210> SEQ ID NO 14
<211> LENGTH: 16
<212> TYPE: DNA
<213> ORGANISM: Artificial Sequence
<220> FEATURE:
<223> OTHER INFORMATION: Nur77 fwd6 primer

```
<400> SEQUENCE: 14
cctgccttcg cctgcc                                                    16

<210> SEQ ID NO 15
<211> LENGTH: 20
<212> TYPE: DNA
<213> ORGANISM: Artificial Sequence
<220> FEATURE:
<223> OTHER INFORMATION: Nur77 rvr2 primer

<400> SEQUENCE: 15
actgtgcgct tgaagaagcc                                                20

<210> SEQ ID NO 16
<211> LENGTH: 21
<212> TYPE: DNA
<213> ORGANISM: Artificial Sequence
<220> FEATURE:
<223> OTHER INFORMATION: Nur77 rvr3 primer

<400> SEQUENCE: 16
agacgtgctc cttcaggcag c                                              21

<210> SEQ ID NO 17
<211> LENGTH: 21
<212> TYPE: DNA
<213> ORGANISM: Artificial Sequence
<220> FEATURE:
<223> OTHER INFORMATION: Nur77 rvr4 primer

<400> SEQUENCE: 17
cacgtccccg gcatcttcct t                                              21

<210> SEQ ID NO 18
<211> LENGTH: 21
<212> TYPE: DNA
<213> ORGANISM: Artificial Sequence
<220> FEATURE:
<223> OTHER INFORMATION: Nur77 rvr5 primer

<400> SEQUENCE: 18
tctgtccgga caacttcctt c                                              21

<210> SEQ ID NO 19
<211> LENGTH: 21
<212> TYPE: DNA
<213> ORGANISM: Artificial Sequence
<220> FEATURE:
<223> OTHER INFORMATION: Nur77 rvr6 primer

<400> SEQUENCE: 19
tgggcagttg ctctgtccat g                                              21

<210> SEQ ID NO 20
<211> LENGTH: 9
<212> TYPE: DNA
<213> ORGANISM: Artificial Sequence
<220> FEATURE:
<223> OTHER INFORMATION: DNA linker encoding Ala, Arg, and Glu

<400> SEQUENCE: 20 gctcgagaa                                                             9
```